United States Patent
Liu et al.

(10) Patent No.: US 11,806,332 B2
(45) Date of Patent: Nov. 7, 2023

(54) COMPOSITIONS AND METHODS FOR INHIBITION OF SARS-COV-2 VIRAL INFECTIONS

(71) Applicant: THE TEXAS A&M UNIVERSITY SYSTEM, College Station, TX (US)

(72) Inventors: Wenshe Liu, College Station, TX (US); Kai Yang, College Station, TX (US); Erol Vatansever, College Station, TX (US); Shiqing Xu, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 17/748,351

(22) Filed: May 19, 2022

(65) Prior Publication Data
US 2022/0273616 A1   Sep. 1, 2022

Related U.S. Application Data

(63) Continuation of application No. PCT/US2020/041179, filed on Jul. 8, 2020.

(60) Provisional application No. 63/027,566, filed on May 20, 2020.

(51) Int. Cl.
| | | |
|---|---|---|
| A61K 31/40 | (2006.01) | |
| A61K 31/14 | (2006.01) | |
| A61P 31/14 | (2006.01) | |
| A61K 31/4515 | (2006.01) | |
| A61K 31/454 | (2006.01) | |

(52) U.S. Cl.
CPC ............ *A61K 31/40* (2013.01); *A61K 31/454* (2013.01); *A61K 31/4515* (2013.01); *A61P 31/14* (2018.01)

(58) Field of Classification Search
CPC ................................ A61K 31/40; A61K 31/14
See application file for complete search history.

(56) References Cited

U.S. PATENT DOCUMENTS

2006/0019967 A1   1/2006  Wu et al.

OTHER PUBLICATIONS

Webpage printout of https://globalrph.com/drugs/calcium-channel-blockers/, 2017, pp. 1-13, accessed Sep. 27, 2022. (Year: 2017).*
Anand et al. SCIENCE vol. 300 Jun. 13, 2003, pp. 1763-1767 (Year: 2003).*
Nguyen et al, BioRxIV, published Feb. 5, 2020, pp. 1-13. (Year: 2020).*
Bodi, Ilona et al., "The L-type calcium channel in the heart: the beat goes on," The Journal of Clinical Investigation, Dec. 2005, pp. 3306-3317, vol. 115.

(Continued)

*Primary Examiner* — Craig D Ricci
*Assistant Examiner* — Janet L Coppins
(74) *Attorney, Agent, or Firm* — BARNES & THORNBURG LLP

(57) ABSTRACT

The present disclosure provides methods of treating COVID-19 by administering a pharmaceutical composition providing inhibition of severe acute respiratory syndrome-coronavirus 2 (SARS-CoV-2) main protease ($M^{Pro}$) in a patient. The disclosure also provides other methods as well as pharmaceutical formulations for use in treating COVID-19 patients.

7 Claims, 12 Drawing Sheets

(56) References Cited

OTHER PUBLICATIONS

Liu, Henry et al., "Cardiovascular Pharmacology: An Update," Anesthesiology Clin, 2010, pp. 723-738, 28.
Li, Yu et al., "Bepridil opens the regulatory N-terminal lobe of cardiac troponin C," PNAS, May 9, 2000, pp. 5140-5145, vol. 97.
MacLachlan, Lesley K et al., "Binding of a Calcium Sensitizer, Bebridil, to Cardiac Troponin C," The Journal of Biological Chemistry, 1990, pp. 9764-9770, vol. 265.
Shree, et al., "Targeting COVID-19 (SARS-COV-2) main protease through active phytochemicals 1-46 of ayurvedic medicinal plants Withania somnifera (Ashwagandha), Tinospora cordifolia (Giloy) and Ocimum sanctum (Tulsi) a molecular docking study", Aug. 27, 2020 (Aug. 27, 2020), Journal of Biomolecular Structure and Dynamics, DOI: 10.1080/07391102.2020.1810778.
Zhou, et al., "Potential Therapeutic Agents and Associated Bioassay Data for COVID-19 and 1-46 Related Human Coronavirus Infections" Jul. 30, 2020 (Jul. 30, 2020), ACS Pharmacology & Translational Science Article ASAP DOI: 10.1021/acsptsci.Oc00074.
Rabaan, et al., "SARS-COV-2/COVID-19 and Advances in Developing Potential Therapeutics 1-46 and Vaccines to Counter this Emerging Pandemic Virus A Review", Apr. 7, 2020 (Apr. 7, 2020), Preprints 2020, 2020040075 DOI: 10.20944/preprints202004.0075. v1.
Joshi, et al., "Discovery of potential multi-target-directed ligands by targeting host-specific SARS- 1-46 CoV-2 structurally conserved main protease", May 5, 2020 (May 5, 2020), Journal of Biomolecular Structure and Dynamics, DOI: 10.1080/07391102.2020. 1760137.
PCT International Search Report and Written Opinion prepared for PCT/US2020/041179, dated Sep. 15, 2020.

\* cited by examiner

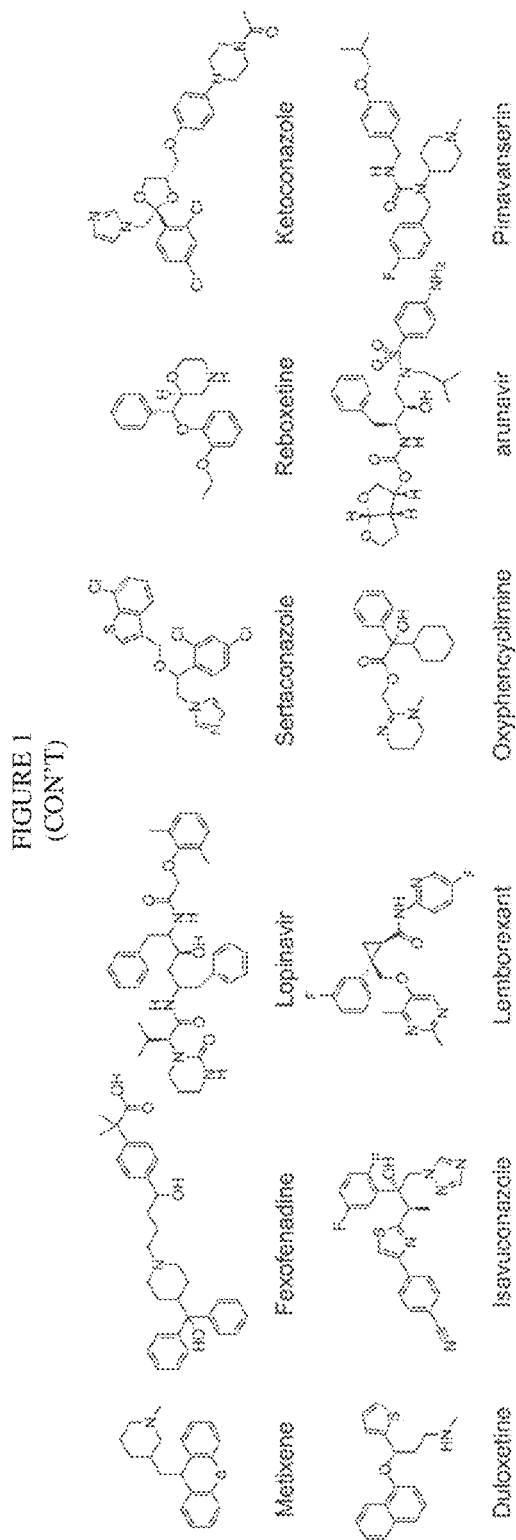
FIGURE 1 (CON'T)

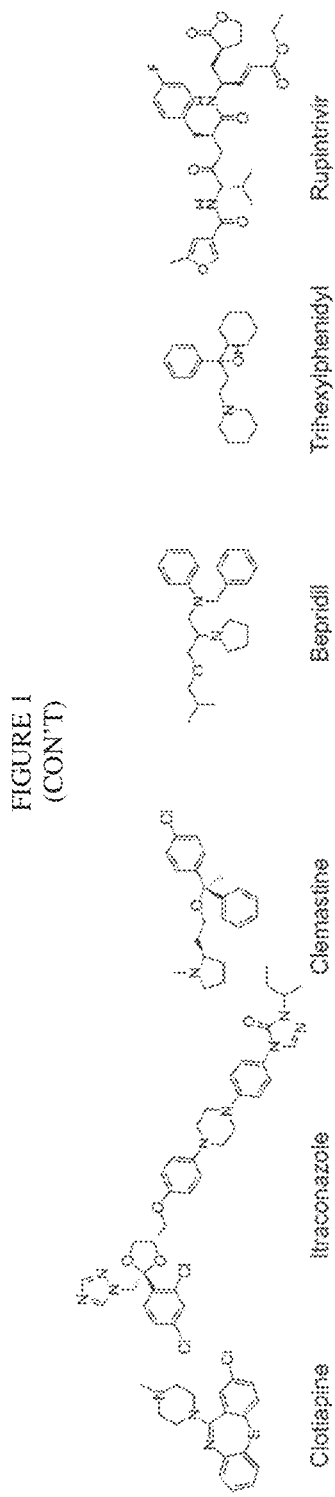
FIGURE 1 (CON'T)

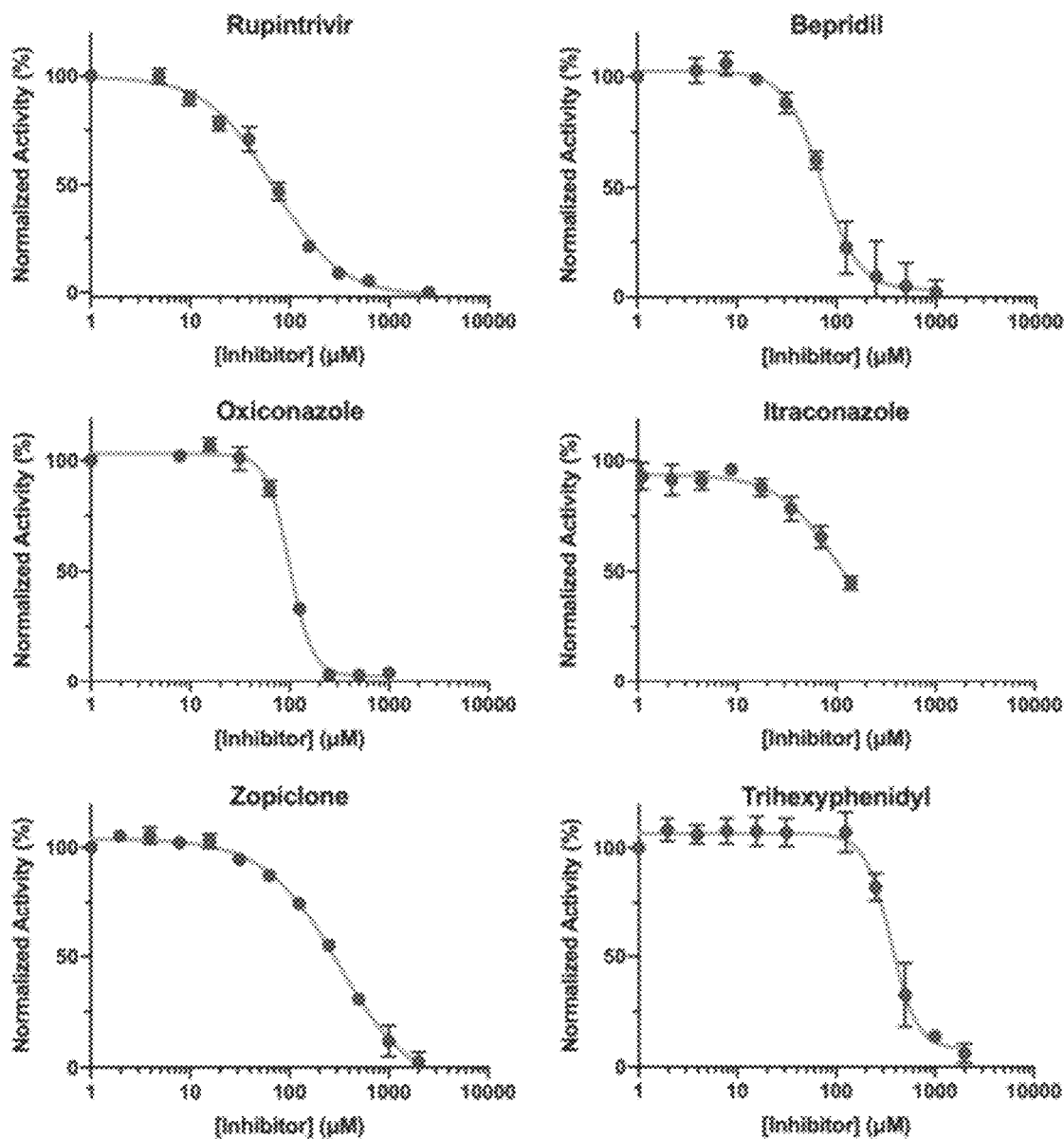
FIGURE 4 (CON'T)

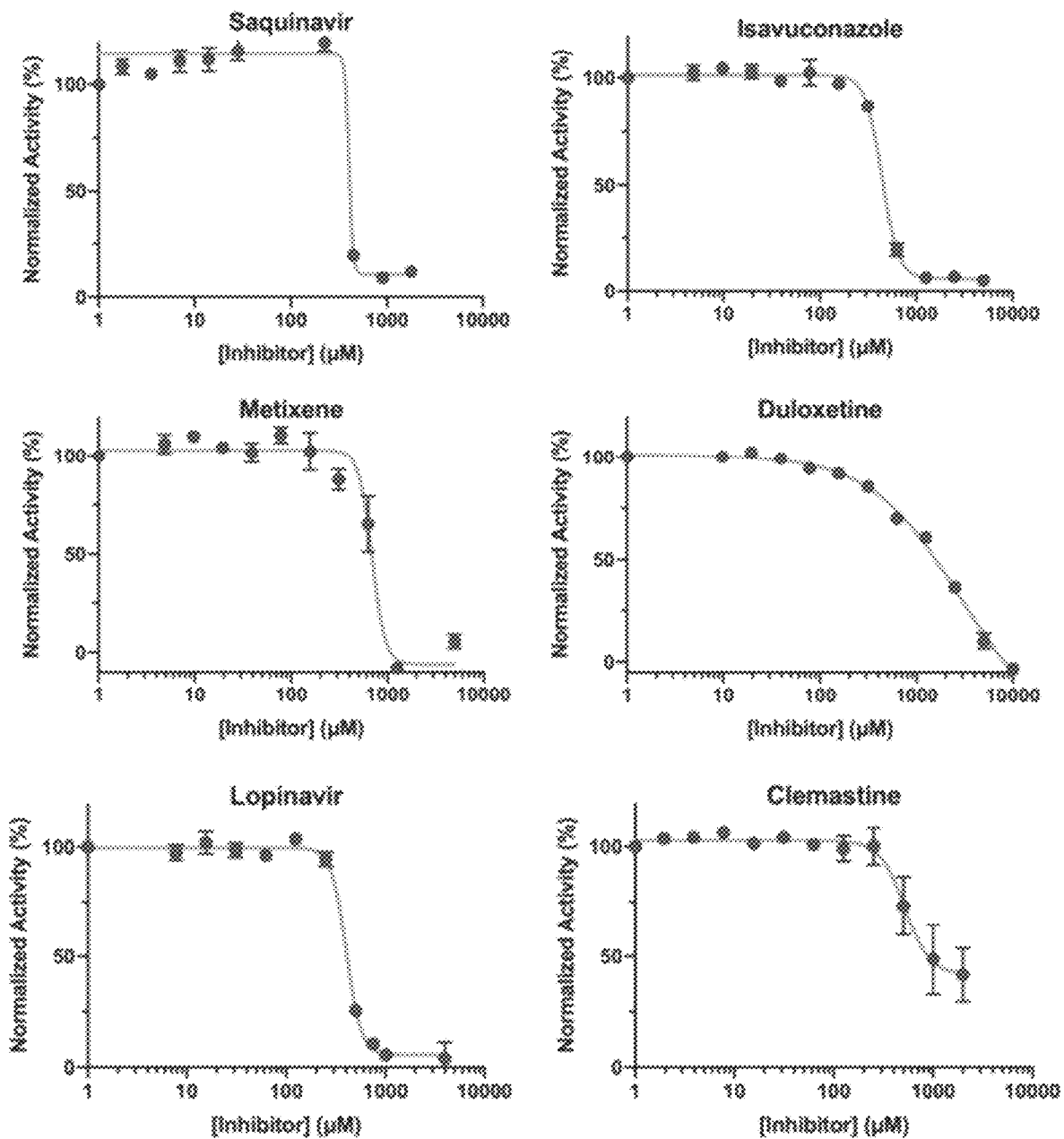
FIGURE 4 (CON'T)

COMPOSITIONS AND METHODS FOR INHIBITION OF SARS-COV-2 VIRAL INFECTIONS

CROSS-REFERENCE TO RELATED APPLICATIONS

This application is a continuation of International Application no. PCT/US2020/41179, filed on Jul. 8, 2020, which claims priority to U.S. Provisional Application Ser. No. 63/027,566, filed on May 20, 2020, the disclosures of which are expressly incorporated by reference herein.

TECHNICAL FIELD

The invention relates to compositions and methods for the treatment of coronavirus infections in patients. In particular, the invention is directed to compositions and methods for the treatment of SARS-CoV-2 infection in patients, also known as COVID-19 disease.

BACKGROUND AND SUMMARY OF THE INVENTION

The COVID-19 pandemic, caused by viral infection with severe acute respiratory syndrome-coronavirus 2 (SARS-CoV-2), has profoundly impacted the entire world. As of July 2020, the total worldwide number of COVID-19 cases had surpassed 10 million and over 500,000 people have died as a result of SARS-CoV-2 infection.

The use of effective treatment regimens is tremendously important to alleviate catastrophic damages caused by SARS-CoV-2. However, the identification of possible therapeutic compositions is challenging due to the novelty of SARS-CoV-2 and the infectious nature of the virus and the high fatality rates associated with infected individuals. At the time of the present disclosure, only remdesivir has been authorized for treatment of patients affected with COVID-19, with approvals for emergency use in the United States as well as in Japan and in Europe for patients with severe COVID-19-related symptoms such as pneumonia.

Therefore, there exists an urgent need for compositions and methods that are efficacious in treating SARS-CoV-2 infection and COVID-19 disease. Our identification of four SARS-CoV-2 essential proteins, including Spike, RNA-dependent RNA polymerase, the main protease ($M^{Pro}$), and papain-like protease, provides possible drug targets for the development of anti-COVID-19 therapeutics. Among the essential proteins, the present disclosure evaluates compositions and methods directed to inhibition of $M^{Pro}$ (previously identified as 3C-like protease ($3CL^{Pro}$)).

$M^{Pro}$ is a cysteine protease that processes itself and then cleaves a number of nonstructural viral proteins from two polypeptide translates that are made from viral RNA in the human cell host. It is believed that the relatively large active site pocket of $M^{Pro}$ as well as a highly nucleophilic, catalytic cysteine residue make $M^{Pro}$ likely to be inhibited by therapeutic agents.

The present disclosure provides compositions and methods for treatment of COVID-19 disease in patients. In particular, the compositions and methods disclosed herein are effective in treating SARS-CoV-2 infection, for example via mechanisms targeting the inhibition of $M^{Pro}$. Furthermore, the present disclosure provides compositions and methods that can target the inhibition of cytopathogenic effect (CPE) induced by SARS-CoV-2 virus, likely by increasing the endosomal pH. As disclosed herein, the compositions and methods disease can successfully target one or more of these mechanisms and provide desperately-needed new therapies for COVID-19 patients.

BRIEF DESCRIPTION OF THE DRAWINGS

FIG. 2A shows the structures of three substrates utilized in the assays (Sub1, Sub2, and Sub3). FIG. 2B shows the activity of 50 nM $M^{Pro}$ on 10 µM Sub1. FIG. 2C shows the activity of 50 nM $M^{Pro}$ on 10 µM Sub2 and Sub3, with normalized florescence signals are normalized for comparison. FIG. 2D shows the activity of different concentrations of $M^{Pro}$ on 10 µM Sub3.

FIG. 5A shows the docking result of pimozide (A) in the active site of $M^{Pro}$. FIG. 5B shows the docking result of ebastine in the active site of $M^{Pro}$. FIG. 5C shows the docking result of bepridil in the active site of $M^{Pro}$. FIG. 5D shows the overlay of the three tested compositions in the active site of $M^{Pro}$. The protein surface topography in FIG. 5A, FIG. 5B, and FIG. 5C is presented to show the concaved active site.

Figure 1:
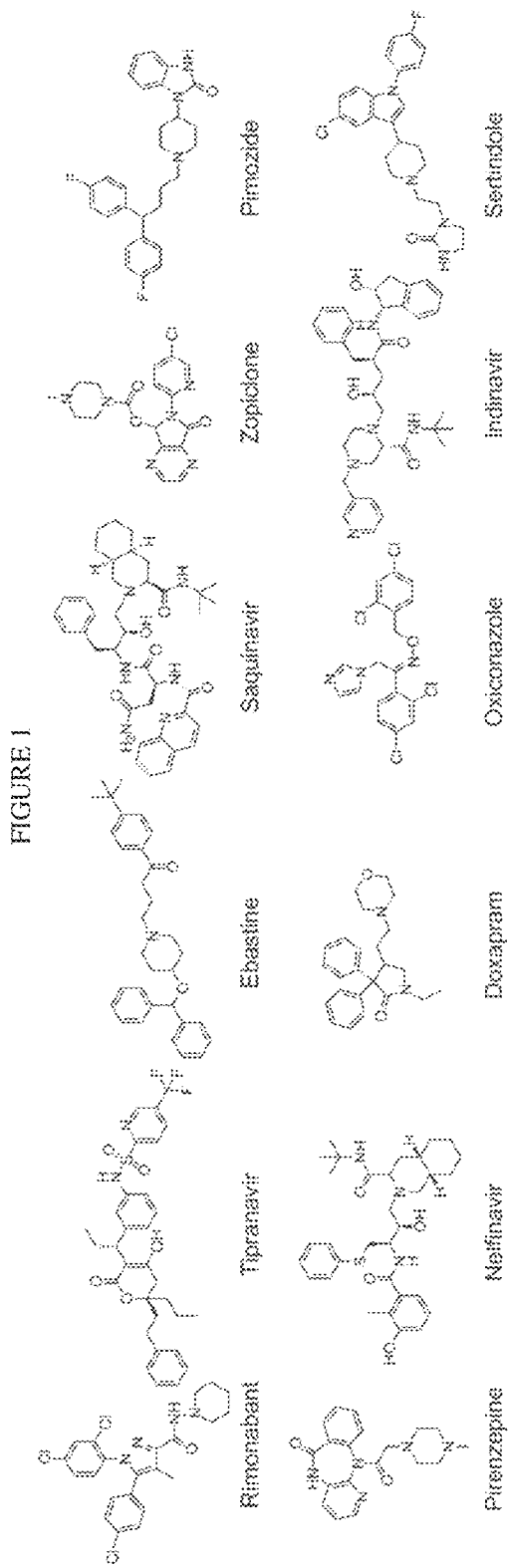
FIG. 1 shows the structures of the various compositions evaluated for inhibition of $M^{Pro}$.
Figure 2A:
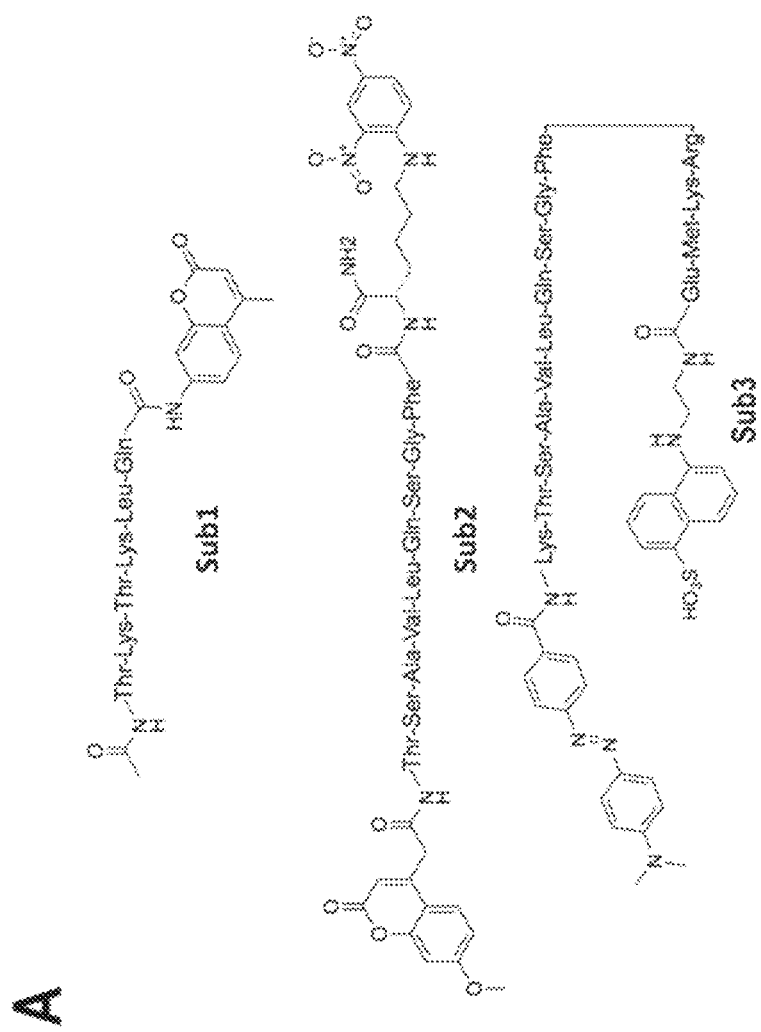
FIGS. 2A-2D show the results of the $M^{Pro}$ inhibition assays.
Figure 2B:
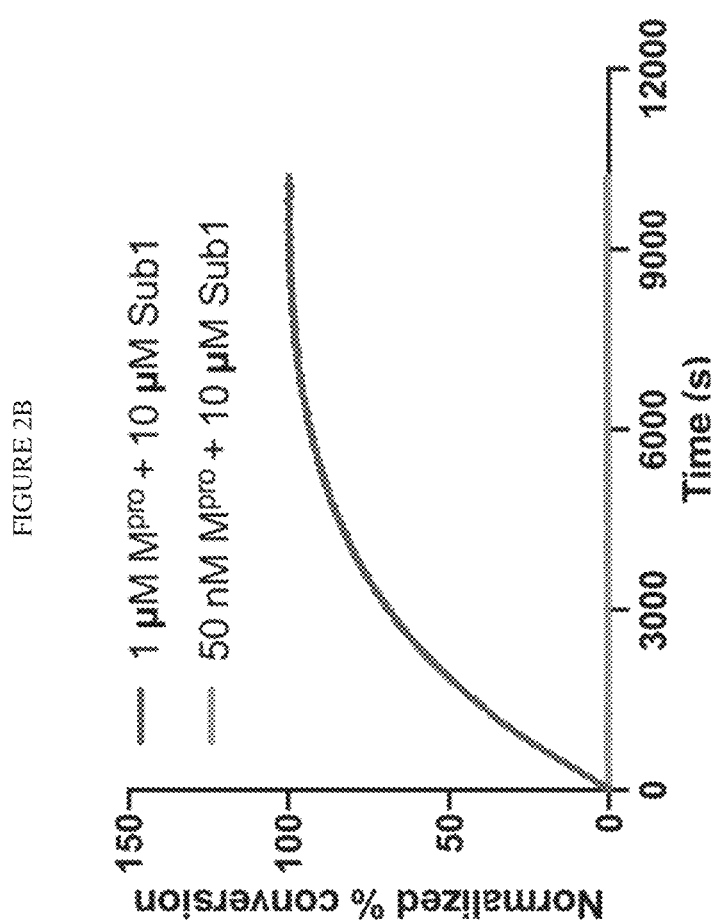
Figure 2C:
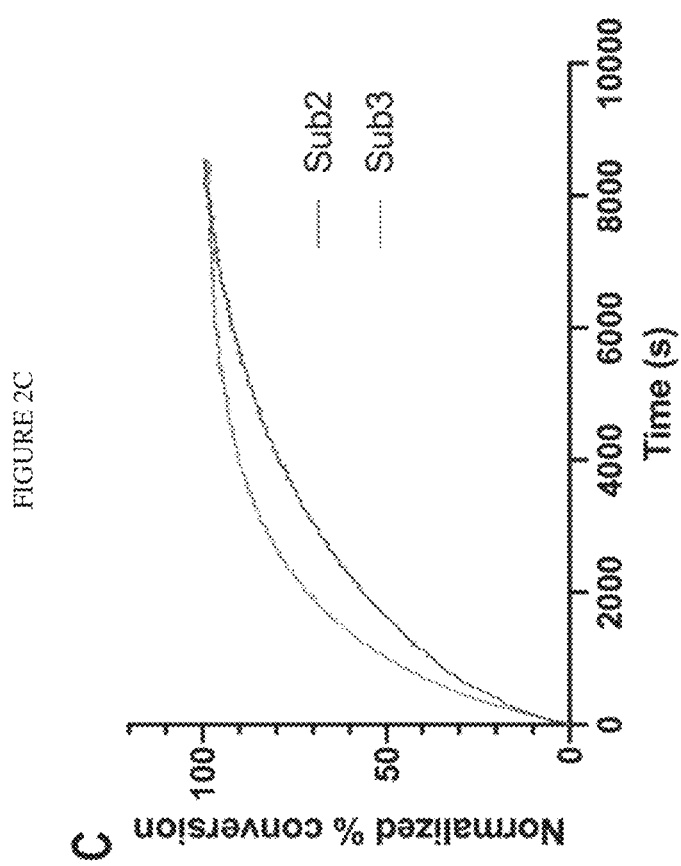
Figure 2D:
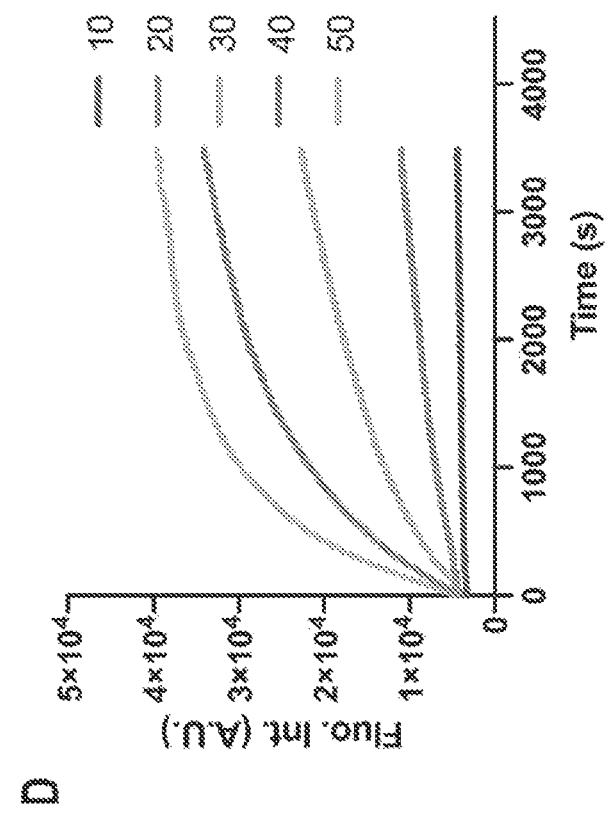

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Various embodiments of the invention are described herein as follows. In an aspect, a method of treating COVID-19 in a patient in need thereof is provided. The method comprises the step of administering a pharmaceutical composition to the patient, wherein the pharmaceutical composition provides inhibition of severe acute respiratory syndrome-coronavirus 2 (SARS-CoV-2) main protease ($M^{Pro}$).

In an aspect, a second method of treating COVID-19 in a patient in need thereof is provided. The second method comprises the step of administering a pharmaceutical composition to the patient, wherein the pharmaceutical composition provides inhibition of severe acute respiratory syndrome-coronavirus 2 (SARS-CoV-2) main protease ($M^{Pro}$) and wherein the pharmaceutical composition provides an increase in endosomal pH in one or more cells of the patient.

In an aspect, a method of inhibiting severe acute respiratory syndrome-coronavirus 2 (SARS-CoV-2) main protease ($M^{Pro}$) in a patient infected with SARS-CoV-2 is provided. The method comprises the step of administering a pharmaceutical composition to the patient, wherein the pharmaceutical composition provides inhibition of SARS-CoV-2 $M^{Pro}$.

In an aspect, a method of treating a coronavirus infection in a patient is provided. The method comprises the step of administering a pharmaceutical composition to the patient.

In an aspect, a pharmaceutical formulation for use in treating a COVID-19 patient is provided. The pharmaceutical formulation comprises a therapeutically effective amount of a compound that inhibits severe acute respiratory syndrome-coronavirus 2 (SARS-CoV-2) main protease ($M^{Pro}$).

An embodiment provides a method of treating COVID-19 in a patient in need thereof, said method comprising the step of administering a pharmaceutical composition to the patient, wherein the pharmaceutical composition provides inhibition of severe acute respiratory syndrome-coronavirus 2 (SARS-CoV-2) main protease ($M^{Pro}$). As used herein, the term "treat" or variations thereof such as "treatment" shall be taken to mean a treatment that ameliorates, reduces, or inhibits a symptom caused by an infection, or prevents or reduces the severity of one or more symptoms of a viral infection. It is to be understood that such treatment therefore includes the prophylaxis of a viral infection in so far as it prevents or reduces symptom development in an infected individual and/or prevents development of a complication thereof.

In some aspects, COVID-19 in the patient is caused by infection of the patient with SARS-CoV-2. In some aspects, COVID-19 in the patient is caused by infection of the patient with a mutation of SARS-CoV-2. Viruses capable of causing infections are known in the art to be susceptible to mutations.

In some aspects, the patient is a human patient. In some aspects, the patient has severe COVID-19-related symptoms. COVID-19-related symptoms include, but are not limited to, fever or chills, cough, shortness of breath or difficulty breathing, fatigue, muscle or body aches, headache, loss of taste or smell, sore throat, congestion or runny nose, nausea or vomiting, and diarrhea. In some aspects, the patient has mild COVID-19-related symptoms. In some aspects, the patient is asymptomatic for COVID-19-related symptoms but has been infected with SARS-CoV-2. In some aspects, the patient is at high risk for infection with SARS-CoV-2.

In some aspects, the treatment is a prophylactic treatment of the patient prior to infection with SARS-CoV-2. As used herein, the term "prophylactic" refers to either preventing or inhibiting the development of a clinical condition or disorder or delaying the onset of a pre-clinically evident stage of a clinical condition or disorder. The term is to be understood as meaning that the compositions according to the present invention can be applied before symptoms of the infection are manifest. The compounds according to the present invention can, for example, be used in a prophylactic treatment. In some aspects, the methods and compositions herein can be used prophylactically to prevent and/or mitigate effects in a patients at risk of infection or susceptible to development of lung disease if infected with a coronavirus (e.g., COVID-19). Patients include the elderly, obese subjects, diabetics, those with afflicted with preconditions (e.g., cancer patients, sarcoid patients, etc.) as well as immuno-suppressed subjects.

In some aspects, the pharmaceutical composition provides an increase in endosomal pH in one or more cells of the patient. For instance, the pharmaceutical compositions can increase cellular endosomal pH, thus targeting the inhibition of cytopathogenic effect (CPE) induced by SARS-CoV-2 virus.

As used herein, the term "administering" refers to any suitable means of delivering the pharmaceutical composition of the present disclosure a patient. In some aspects, the administration is a parenteral administration. Suitable routes for such parenteral administration include intravenous, intraarterial, intraperitoneal, intrathecal, intradermal, epidural, intracerebroventricular, intraurethral, intrasternal, intracranial, intratumoral, intramuscular, and subcutaneous delivery. Suitable means for parenteral administration include needle (including microneedle) injectors, needle-free injectors and infusion techniques. In other embodiments, the administration is an oral administration. The term "oral administration" refers to the provision of the pharmaceutical composition via the mouth through ingestion, or via some other part of the gastrointestinal system including the esophagus. Examples of oral dosage forms include tablets (including compressed, coated or uncoated), capsules, hard or soft gelatin capsules, pellets, pills, powders, granules, elixirs, tinctures, colloidal dispersions, dispersions, effervescent compositions, films, sterile solutions or suspensions, syrups and emulsions and the like.

As used herein, the term "compound" refers to a base of the compound, pharmaceutically acceptable salts of the compound, other salts of the compound, metabolites of the compound, and prodrugs of the compound. The term "pharmaceutically acceptable salt" refers to an addition salt that exists in conjunction with the acidic or basic portion of the compound. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when the compound and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when the compound and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In some aspects, the pharmaceutical composition comprises a compound with a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol. In one aspect, the pharmaceutical composition comprises a compound with a binding energy to MPro at a value of less than −8.0 cal/mol. In one aspect, the pharmaceutical composition comprises a compound with a binding energy to MPro at a value of less than −8.3 cal/mol. In one aspect, the pharmaceutical composition comprises a compound with a binding energy to MPro at a value of less than −8.5 cal/mol. In one aspect, the pharmaceutical composition comprises a compound with a binding energy to MPro at a value of less than −9.0 cal/mol. In one aspect, the pharmaceutical composition comprises a compound with a binding energy to MPro at a value of less than −9.5 cal/mol. In one aspect, the pharmaceutical composition comprises a compound with a binding energy to MPro at a value of less than −10.0 cal/mol.

In some aspects, the pharmaceutical composition comprises a compound with an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

In one aspect, the pharmaceutical composition comprises a compound with an $IC_{50}$ value for inhibition of $M^{Pro}$ of less than 100 μM. In one aspect, the pharmaceutical composition comprises a compound with an $IC_{50}$ value for inhibition of $M^{Pro}$ of less than 80 μM. In one aspect, the pharmaceutical composition comprises a compound with an $IC_{50}$ value for inhibition of $M^{Pro}$ of less than 70 μM. In one aspect, the pharmaceutical composition comprises a compound with an $IC_{50}$ value for inhibition of $M^{Pro}$ of less than 60 μM. In one aspect, the pharmaceutical composition comprises a compound with an $IC_{50}$ value for inhibition of $M^{Pro}$ of less than 50 μM. In one aspect, the pharmaceutical composition comprises a compound with an $IC_{50}$ value for inhibition of $M^{Pro}$ of less than 40 μM.

In some aspects, the compound provides inhibition of SARS-CoV-2-induced cytopathogenic effect (CPE). As described herein, compounds of the present disclosure can inhibit cytopathogenic effect induced by SARS-CoV-2 in Vero E6 cells completely and at dose-dependent levels, and inhibit cytopathogenic effect induced by SARS-CoV-2 in ACE2-expressing A549 cells completely and at dose-dependent levels. In some aspects, the inhibition of SARS-CoV-2-induced CPE is dose dependent. In some aspects, the inhibition of SARS-CoV-2-induced CPE is about 100%.

In some aspects, the pharmaceutical composition comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

In some aspects, the pharmaceutical composition comprises a compound selected from the group consisting of pimozide, ebastine, rupintrivir, bepridil, sertaconazole, rimonabant, and oxiconazole. In some aspects, the pharmaceutical composition comprises a compound selected from the group consisting of pimozide, ebastine, and bepridil.

In some aspects, the pharmaceutical composition comprises a compound that is bepridil. Bepridil is a calcium channel blocker and has a chemical structure of:

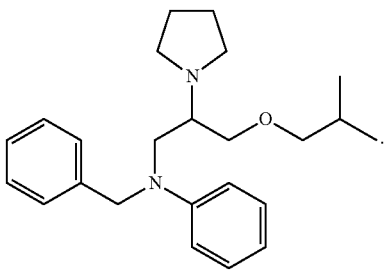 [SMILES: CC(C)COCC(CN(Cc1ccccc1)c1ccccc1)N1CCCC1]

In some aspects, the pharmaceutical composition comprises a compound that is pimozide. Pimozide is a compound of the diphenylbutylpiperidine class and has a chemical structure of:

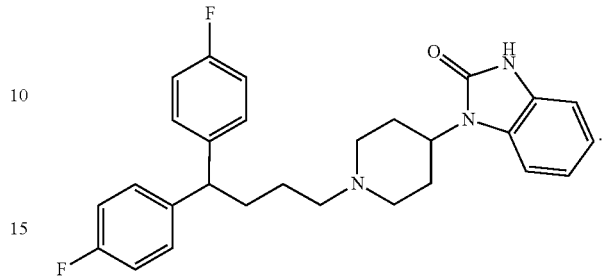

In some aspects, the pharmaceutical composition comprises a compound that is ebastine. Ebastine is an $H_1$ antihistamine and has a chemical structure of:

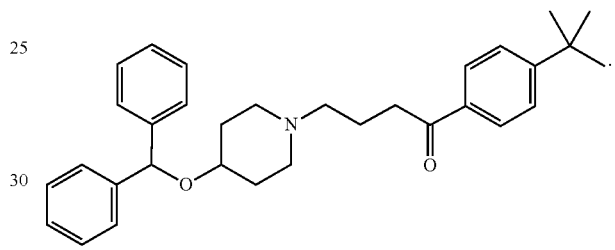

In some aspects, the pharmaceutical composition comprises a compound present at a dose between 0.001 to 2000 mg. A skilled artisan can determine the dose of a compound described herein to provide a therapeutically effective amount to the patient. As used herein, the term "therapeutically effective amount" refers to an amount which gives the desired benefit to a patient and includes both treatment and prophylactic administration. The amount will vary from one patient to another and will depend upon a number of factors, including the overall physical condition of the patient and the underlying cause of the condition to be treated. As used herein, the term "patient" refers to an animal, for example a human.

In some aspects, the pharmaceutical composition comprises a compound present at a dose between 1 to 2000 mg. In some aspects, the pharmaceutical composition comprises a compound present at a dose between 5 to 1500 mg. In some aspects, the pharmaceutical composition comprises a compound present at a dose between 10 to 1000 mg. In some aspects, the pharmaceutical composition comprises a compound present at a dose between 100 to 800 mg. In some aspects, the pharmaceutical composition comprises a compound present at a dose between 200 to 600 mg. In some aspects, the pharmaceutical composition comprises a compound present at a dose of 200 mg. In some aspects, the pharmaceutical composition comprises a compound present at a dose of 300 mg. In some aspects, the pharmaceutical composition comprises a compound present at a dose of 400 mg. In some aspects, the pharmaceutical composition comprises a compound present at a dose of 500 mg. In some aspects, the pharmaceutical composition comprises a compound present at a dose of 600 mg.

In some aspects, the pharmaceutical composition comprises a compound present at a dose between 0.001 to 1000 mg of the compound per kg of patient body weight. A skilled artisan can determine the dose of a compound described herein to provide a therapeutically effective amount to the patient. In some aspects, the pharmaceutical composition comprises a compound present at a dose between 0.001 to 100 mg of the compound per kg of patient body weight. In some aspects, the pharmaceutical composition comprises a compound present at a dose between 0.01 to 100 mg of the compound per kg of patient body weight. In some aspects, the pharmaceutical composition comprises a compound present at a dose between 0.1 to 100 mg of the compound per kg of patient body weight. In some aspects, the pharmaceutical composition comprises a compound present at a dose between 0.1 to 10 mg of the compound per kg of patient body weight. In some aspects, the pharmaceutical composition comprises a compound present at a dose between 1 to 5 mg of the compound per kg of patient body weight. In some aspects, the pharmaceutical composition comprises a compound present at a dose of 2 mg of the compound per kg of patient body weight. In some aspects, the pharmaceutical composition comprises a compound present at a dose of 3 mg of the compound per kg of patient body weight. In some aspects, the pharmaceutical composition comprises a compound present at a dose of 4 mg of the compound per kg of patient body weight. In some aspects, the pharmaceutical composition comprises a compound present at a dose of 5 mg of the compound per kg of patient body weight.

In some aspects, the method further comprises administration of a second therapeutic agent to the patient. The second therapeutic agent can comprise a compound disclosed herein or a compound, pharmaceutical, or other chemical entity that is shown to be therapeutically effective in treating COVID-19 and/or SARS-CoV-2 infection in the patient. Furthermore, the second therapeutic agent can comprise a compound disclosed herein or a compound, pharmaceutical, or other chemical entity that is therapeutically effective in treating a symptom associated with COVID-19 and/or SARS-CoV-2 infection in the patient.

An embodiment provides a second method of treating COVID-19 in a patient in need thereof, said method comprising the step of administering a pharmaceutical composition to the patient, wherein the pharmaceutical composition provides inhibition of severe acute respiratory syndrome-coronavirus 2 (SARS-CoV-2) main protease ($M^{Pro}$) and wherein the pharmaceutical composition provides an increase in endosomal pH in one or more cells of the patient. The previously described aspects of the method of treating COVID-19 in a patient in need thereof are applicable to the second method of treating COVID-19 in a patient in need thereof described herein.

An embodiment provides a method of inhibiting severe acute respiratory syndrome-coronavirus 2 (SARS-CoV-2) main protease ($M^{Pro}$) in a patient infected with SARS-CoV-2, said method comprising the step of administering a pharmaceutical composition to the patient, wherein the pharmaceutical composition provides inhibition of SARS-CoV-2 $M^{Pro}$. The previously described aspects of the method of treating COVID-19 in a patient in need thereof are applicable to the method of inhibiting severe acute respiratory syndrome-coronavirus 2 (SARS-CoV-2) main protease ($M^{Pro}$) in a patient infected with SARS-CoV-2 described herein.

An embodiment provides a method of treating a coronavirus infection in a patient, said method comprising the step of administering a pharmaceutical composition to the patient. In an aspect, wherein the coronavirus infection is an infection caused by SARS-CoV-2. In an aspect, the coronavirus infection is an infection caused by a SARS-CoV-2 mutation. In an aspect, the pharmaceutical composition provides inhibition of SARS-CoV-2 $M^{Pro}$. In an aspect, the pharmaceutical composition provides an increase in endosomal pH in one or more cells of the patient. In an aspect, the pharmaceutical composition provides inhibition of SARS-CoV-2 $M^{Pro}$ and the pharmaceutical composition provides an increase in endosomal pH in one or more cells of the patient.

In some aspects, the patient is a human patient. In some aspects, the patient has severe coronavirus-related symptoms. In some aspects, the patient has mild coronavirus-related symptoms. In some aspects, the patient is asymptomatic for coronavirus-related symptoms but has been infected with coronavirus. In some aspects, the patient is at high risk for infection with coronavirus. In some aspects, the treatment is a prophylactic treatment of the patient prior to infection with coronavirus.

The previously described aspects of the method of treating COVID-19 in a patient in need thereof are applicable to the method of treating a coronavirus infection in a patient described herein.

An embodiment provides a pharmaceutical formulation for use in treating a COVID-19 patient, said pharmaceutical formulation comprising a therapeutically effective amount of a compound that inhibits severe acute respiratory syndrome-coronavirus 2 (SARS-CoV-2) main protease ($M^{Pro}$). In some aspects, COVID-19 is caused by infection with SARS-CoV-2. In some aspects, COVID-19 is caused by infection with a mutation of SARS-CoV-2.

In some aspects, the patient is a human patient. In some aspects, the pharmaceutical formulation is adapted for treatment of a patient with severe COVID-19-related symptoms. In some aspects, the pharmaceutical formulation is adapted for treatment of a patient with mild COVID-19-related symptoms. In some aspects, the pharmaceutical formulation is adapted for treatment of a patient that is asymptomatic for coronavirus-related symptoms but has been infected with SARS-CoV-2. In some aspects, the pharmaceutical formulation is adapted for treatment of a patient at high risk for infection with SARS-CoV-2. In some aspects, the pharmaceutical formulation is adapted for treatment of a patient prior to infection with SARS-CoV-2.

In some aspects, the pharmaceutical formulation is an oral formulation. In some aspects, the oral formulation is selected from the group consisting of tablets, capsules, hard or soft gelatin capsules, pellets, pills, powders, granules, elixirs, tinctures, colloidal dispersions, dispersions, effervescent compositions, films, sterile solutions, sterile suspensions, syrups, and emulsions. In some aspects, the pharmaceutical formulation is a parenteral formulation. In some aspects, the parenteral formulation is selected from the group consisting of intravenous, intraarterial, intraperitoneal, intrathecal, intradermal, epidural, intracerebroventricular, intraurethral, intrasternal, intracranial, intratumoral, intramuscular, and subcutaneous.

In some aspects, the pharmaceutical formulation comprises a compound that has a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol. In some aspects, the compound has a binding energy to $M^{Pro}$ at a value of less than −8.0 cal/mol. In some aspects, the the compound has a binding energy to $M^{Pro}$ at a value of less than −8.3 cal/mol. In some aspects, the compound has a binding energy to $M^{Pro}$ at a value of less than −8.5 cal/mol. In some aspects, the compound has a binding energy to $M^{Pro}$ at a value of less than −9.0 cal/mol. In some aspects, the compound has a binding energy to $M^{Pro}$ at a value of less than −9.5 cal/mol. In some aspects, the compound has a binding energy to $M^{Pro}$ at a value of less than −10.0 cal/mol.

In some aspects, the pharmaceutical formulation comprises a compound that has an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

In one aspect, the pharmaceutical formulation comprises a compound with an $IC_{50}$ value for inhibition of $M^{Pro}$ of less than 100 μM. In one aspect, the pharmaceutical formulation comprises a compound with an $IC_{50}$ value for inhibition of $M^{Pro}$ of less than 80 μM. In one aspect, the pharmaceutical formulation comprises a compound with an $IC_{50}$ value for inhibition of $M^{Pro}$ of less than 70 μM. In one aspect, the pharmaceutical formulation comprises a compound with an $IC_{50}$ value for inhibition of $M^{Pro}$ of less than 60 μM. In one aspect, the pharmaceutical formulation comprises a compound with an $IC_{50}$ value for inhibition of $M^{Pro}$ of less than 50 μM. In one aspect, the pharmaceutical formulation comprises a compound with an $IC_{50}$ value for inhibition of $M^{Pro}$ of less than 40 μM.

In some aspects, the pharmaceutical formulation comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

In some aspects, the pharmaceutical formulation comprises a compound selected from the group consisting of pimozide, ebastine, rupintrivir, bepridil, sertaconazole, rimonabant, and oxiconazole. In some aspects, the pharmaceutical formulation comprises a compound selected from the group consisting of pimozide, ebastine, and bepridil.

In some aspects, the pharmaceutical formulation comprises a compound that is bepridil. Bepridil is a calcium channel blocker and has a chemical structure of:

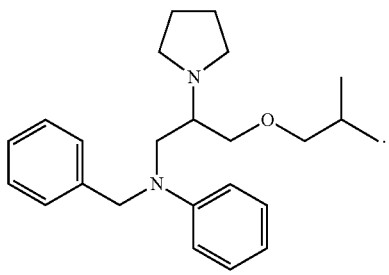

In some aspects, the pharmaceutical formulation comprises a compound that is pimozide. Pimozide is a compound of the diphenylbutylpiperidine class and has a chemical structure of:

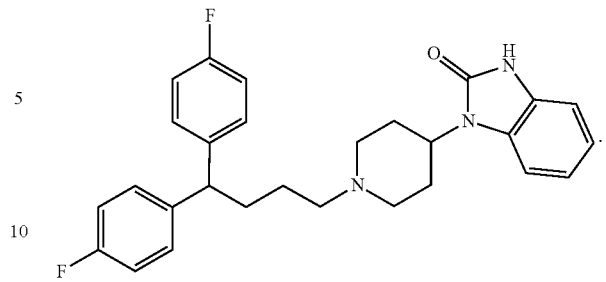

In some aspects, the pharmaceutical formulation comprises a compound that is ebastine. Ebastine is an $H_1$ antihistamine and has a chemical structure of:

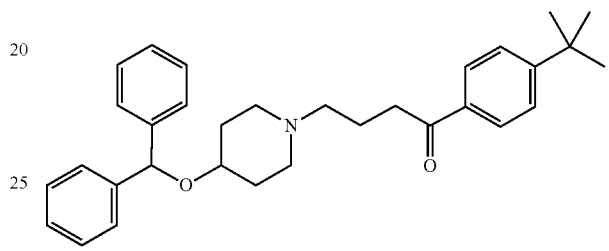

In some aspects, the pharmaceutical formulation comprises a compound present at a dose between 0.001 to 2000 mg. A skilled artisan can determine the dose of a compound described herein to provide a therapeutically effective amount to the patient. As used herein, the term "therapeutically effective amount" refers to an amount which gives the desired benefit to a patient and includes both treatment and prophylactic administration. The amount will vary from one patient to another and will depend upon a number of factors, including the overall physical condition of the patient and the underlying cause of the condition to be treated. As used herein, the term "patient" refers to an animal, for formulation a human.

In some aspects, the pharmaceutical composition comprises a compound present at a dose between 1 to 2000 mg. In some aspects, the pharmaceutical formulation comprises a compound present at a dose between 5 to 1500 mg. In some aspects, the pharmaceutical formulation comprises a compound present at a dose between 10 to 1000 mg. In some aspects, the pharmaceutical formulation comprises a compound present at a dose between 100 to 800 mg. In some aspects, the pharmaceutical formulation comprises a compound present at a dose between 200 to 600 mg. In some aspects, the pharmaceutical formulation comprises a compound present at a dose of 200 mg. In some aspects, the pharmaceutical formulation comprises a compound present at a dose of 300 mg. In some aspects, the pharmaceutical formulation comprises a compound present at a dose of 400 mg. In some aspects, the pharmaceutical formulation comprises a compound present at a dose of 500 mg. In some aspects, the pharmaceutical formulation comprises a compound present at a dose of 600 mg.

In some aspects, the pharmaceutical formulation comprises a compound present at a dose between 0.001 to 1000 mg of the compound per kg of patient body weight. A skilled artisan can determine the dose of a compound described herein to provide a therapeutically effective amount to the patient. In some aspects, the pharmaceutical formulation comprises a compound present at a dose between 0.001 to 100 mg of the compound per kg of patient body weight. In some aspects, the pharmaceutical formulation comprises a compound present at a dose between 0.01 to 100 mg of the compound per kg of patient body weight. In some aspects, the pharmaceutical formulation comprises a compound present at a dose between 0.1 to 100 mg of the compound per kg of patient body weight. In some aspects, the pharmaceutical formulation comprises a compound present at a dose between 0.1 to 10 mg of the compound per kg of patient body weight. In some aspects, the pharmaceutical formulation comprises a compound present at a dose between 1 to 5 mg of the compound per kg of patient body weight. In some aspects, the pharmaceutical formulation comprises a compound present at a dose of 2 mg of the compound per kg of patient body weight. In some aspects, the pharmaceutical formulation comprises a compound present at a dose of 3 mg of the compound per kg of patient body weight. In some aspects, the pharmaceutical formulation comprises a compound present at a dose of 4 mg of the compound per kg of patient body weight. In some aspects, the pharmaceutical formulation comprises a compound present at a dose of 5 mg of the compound per kg of patient body weight.

In some aspects, the pharmaceutical formulation is a unit dose. In some aspects, the pharmaceutical formulation is a single unit dose. As used herein, the term "unit dose" is a discrete amount of the composition comprising a predetermined amount of the compound. The amount of the compound is generally equal to a dosage which would be administered to an animal or a convenient fraction of such a dosage such as, for example, one-half or one-third of such a dosage.

In some aspects, the pharmaceutical formulation further comprises a second therapeutic agent. In some aspects, the pharmaceutical formulation is adapted for administration with a second therapeutic agent. The second therapeutic agent can comprise a compound disclosed herein or a compound, pharmaceutical, or other chemical entity that is shown to be therapeutically effective in treating COVID-19 and/or SARS-CoV-2 infection in the patient. Furthermore, the second therapeutic agent can comprise a compound disclosed herein or a compound, pharmaceutical, or other chemical entity that is therapeutically effective in treating a symptom associated with COVID-19 and/or SARS-CoV-2 infection in the patient.

In some aspects, the pharmaceutical formulation further comprises one or more pharmaceutically acceptable carriers. Such pharmaceutically acceptable carriers include those listed in HANDBOOK OF PHARMACEUTICAL EXCIPIENTS, P. J. Sheskey et al. (Eds.), Pharmaceutical Press, 2017 which are known to the skilled artisan.

The following numbered embodiments are contemplated and are non-limiting:

1. A method of treating COVID-19 in a patient in need thereof, said method comprising the step of administering a pharmaceutical composition to the patient, wherein the pharmaceutical composition provides inhibition of severe acute respiratory syndrome-coronavirus 2 (SARS-CoV-2) main protease ($M^{Pro}$).

2. The method of clause 1, any other suitable clause, or any combination of suitable clauses, wherein COVID-19 is caused by infection with SARS-CoV-2.

3. The method of clause 1, any other suitable clause, or any combination of suitable clauses, wherein COVID-19 is caused by infection with a mutation of SARS-CoV-2.

4. The method of clause 1, any other suitable clause, or any combination of suitable clauses, wherein the patient is a human patient.

5. The method of clause 1, any other suitable clause, or any combination of suitable clauses, wherein the patient has severe COVID-19-related symptoms.

6. The method of clause 1, any other suitable clause, or any combination of suitable clauses, wherein the patient has mild COVID-19-related symptoms.

7. The method of clause 1, any other suitable clause, or any combination of suitable clauses, wherein the patient is asymptomatic for COVID-19-related symptoms but has been infected with SARS-CoV-2.

8. The method of clause 1, any other suitable clause, or any combination of suitable clauses, wherein the patient is at high risk for infection with SARS-CoV-2.

9. The method of clause 1, any other suitable clause, or any combination of suitable clauses, wherein the treatment is a prophylactic treatment of the patient prior to infection with SARS-CoV-2.

10. The method of clause 1, any other suitable clause, or any combination of suitable clauses, wherein the pharmaceutical composition provides an increase in endosomal pH in one or more cells of the patient.

11. The method of clause 1, any other suitable clause, or any combination of suitable clauses, wherein the administration is an oral administration.

12. The method of clause 1, any other suitable clause, or any combination of suitable clauses, wherein the administration is a parenteral administration.

13. The method of clause 1, any other suitable clause, or any combination of suitable clauses, wherein the pharmaceutical composition comprises a compound with a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol.

14. The method of clause 1, any other suitable clause, or any combination of suitable clauses, wherein the pharmaceutical composition comprises a compound with a binding energy to $M^{Pro}$ at a value of less than −8.0 cal/mol.

15. The method of clause 1, any other suitable clause, or any combination of suitable clauses, wherein the pharmaceutical composition comprises a compound with a binding energy to $M^{Pro}$ at a value of less than −8.3 cal/mol.

16. The method of clause 1, any other suitable clause, or any combination of suitable clauses, wherein the pharmaceutical composition comprises a compound with a binding energy to $M^{Pro}$ at a value of less than −8.5 cal/mol.

17. The method of clause 1, any other suitable clause, or any combination of suitable clauses, wherein the pharmaceutical composition comprises a compound with a binding energy to $M^{Pro}$ at a value of less than −9.0 cal/mol.

18. The method of clause 1, any other suitable clause, or any combination of suitable clauses, wherein the pharmaceutical composition comprises a compound with a binding energy to $M^{Pro}$ at a value of less than −9.5 cal/mol.

19. The method of clause 1, any other suitable clause, or any combination of suitable clauses, wherein the pharmaceutical composition comprises a compound with a binding energy to $M^{Pro}$ at a value of less than −10.0 cal/mol.

20. The method of clause 1, any other suitable clause, or any combination of suitable clauses, wherein the pharmaceutical composition comprises a compound with an $IC_{50}$ value for inhibition of $M^{Pro}$ selected from the group consisting of less than 100 µM, less than 90 µM, less than 80 µM, less than 70 µM, less than 60 µM, less than 50 µM, and less than 40 µM.

21. The method of clause 1, any other suitable clause, or any combination of suitable clauses, wherein the pharmaceutical composition comprises a compound with an $IC_{50}$ value for inhibition of $M^{Pro}$ of less than 100 µM.

22. The method of clause 1, any other suitable clause, or any combination of suitable clauses, wherein the pharmaceutical composition comprises a compound with an $IC_{50}$ value for inhibition of $M^{Pro}$ of less than 80 µM.

23. The method of clause 1, any other suitable clause, or any combination of suitable clauses, wherein the pharmaceutical composition comprises a compound with an $IC_{50}$ value for inhibition of $M^{Pro}$) of less than 70 µM.

24. The method of clause 1, any other suitable clause, or any combination of suitable clauses, wherein the pharmaceutical composition comprises a compound with an $IC_{50}$ value for inhibition of $M^{Pro}$) of less than 60 µM.

25. The method of clause 1, any other suitable clause, or any combination of suitable clauses, wherein the pharmaceutical composition comprises a compound with an $IC_{50}$ value for inhibition of $M^{Pro}$) of less than 50 µM.

26. The method of clause 1, any other suitable clause, or any combination of suitable clauses, wherein the pharmaceutical composition comprises a compound with an $IC_{50}$ value for inhibition of $M^{Pro}$) of less than 40 µM.

27. The method of clause 1, any other suitable clause, or any combination of suitable clauses, wherein the pharmaceutical composition comprises a compound providing inhibition of SARS-CoV-2-induced cytopathogenic effect (CPE).

28. The method of clause 27, any other suitable clause, or any combination of suitable clauses, wherein the inhibition of SARS-CoV-2-induced CPE is dose dependent.

29. The method of clause 27, any other suitable clause, or any combination of suitable clauses, wherein the inhibition of SARS-CoV-2-induced CPE is about 100%.

30. The method of clause 1, any other suitable clause, or any combination of suitable clauses, wherein the pharmaceutical composition comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

31. The method of clause 1, any other suitable clause, or any combination of suitable clauses, wherein the pharmaceutical composition comprises a compound selected from the group consisting of pimozide, ebastine, rupintrivir, bepridil, sertaconazole, rimonabant, and oxiconazole.

32. The method of clause 1, any other suitable clause, or any combination of suitable clauses, wherein the pharmaceutical composition comprises a compound selected from the group consisting of pimozide, ebastine, and bepridil.

33. The method of clause 1, any other suitable clause, or any combination of suitable clauses, wherein the pharmaceutical composition comprises a compound that is bepridil.

34. The method of clause 1, any other suitable clause, or any combination of suitable clauses, wherein the pharmaceutical composition comprises a compound that is pimozide.

35. The method of clause 1, any other suitable clause, or any combination of suitable clauses, wherein the pharmaceutical composition comprises a compound that is ebastine.

36. The method of clause 1, any other suitable clause, or any combination of suitable clauses, wherein the pharmaceutical composition comprises a compound that is rupintrivir.

37. The method of clause 1, any other suitable clause, or any combination of suitable clauses, wherein the pharmaceutical composition comprises a compound that is sertaconazole.

38. The method of clause 1, any other suitable clause, or any combination of suitable clauses, wherein the pharmaceutical composition comprises a compound that is rimonabant.

39. The method of clause 1, any other suitable clause, or any combination of suitable clauses, wherein the pharmaceutical composition comprises a compound that is oxiconazole.

40. The method of clause 1, any other suitable clause, or any combination of suitable clauses, wherein the pharmaceutical composition comprises a compound that is itraconazole.

41. The method of clause 1, any other suitable clause, or any combination of suitable clauses, wherein the pharmaceutical composition comprises a compound that is tipranavir.

42. The method of clause 1, any other suitable clause, or any combination of suitable clauses, wherein the pharmaceutical composition comprises a compound that is nelfinavir.

43. The method of clause 1, any other suitable clause, or any combination of suitable clauses, wherein the pharmaceutical composition comprises a compound that is zopiclone.

44. The method of clause 1, any other suitable clause, or any combination of suitable clauses, wherein the pharmaceutical composition comprises a compound that is trihexyphenidyl.

45. The method of clause 1, any other suitable clause, or any combination of suitable clauses, wherein the pharmaceutical composition comprises a compound that is saquinavir.

46. The method of clause 1, any other suitable clause, or any combination of suitable clauses, wherein the pharmaceutical composition comprises a compound that is isavuconazole.

47. The method of clause 1, any other suitable clause, or any combination of suitable clauses, wherein the pharmaceutical composition comprises a compound that is lopinavir.

48. The method of clause 1, any other suitable clause, or any combination of suitable clauses, wherein the pharmaceutical composition comprises a compound that is clemastine.

49. The method of clause 1, any other suitable clause, or any combination of suitable clauses, wherein the pharmaceutical composition comprises a compound that is metixene.

50. The method of clause 1, any other suitable clause, or any combination of suitable clauses, wherein the pharmaceutical composition comprises a compound that is duloxetine.

51. The method of clause 1, any other suitable clause, or any combination of suitable clauses, wherein the pharmaceutical composition comprises a compound present at a dose between 0.001 to 2000 mg.

52. The method of clause 1, any other suitable clause, or any combination of suitable clauses, wherein the pharmaceutical composition comprises a compound present at a dose between 1 to 2000 mg.

53. The method of clause 1, any other suitable clause, or any combination of suitable clauses, wherein the pharmaceutical composition comprises a compound present at a dose between 5 to 1500 mg.

54. The method of clause 1, any other suitable clause, or any combination of suitable clauses, wherein the pharmaceutical composition comprises a compound present at a dose between 10 to 1000 mg.

55. The method of clause 1, any other suitable clause, or any combination of suitable clauses, wherein the pharmaceutical composition comprises a compound present at a dose between 100 to 800 mg.

56. The method of clause 1, any other suitable clause, or any combination of suitable clauses, wherein the pharmaceutical composition comprises a compound present at a dose between 200 to 600 mg.

57. The method of clause 1, any other suitable clause, or any combination of suitable clauses, wherein the pharmaceutical composition comprises a compound present at a dose of 200 mg.

58. The method of clause 1, any other suitable clause, or any combination of suitable clauses, wherein the pharmaceutical composition comprises a compound present at a dose of 300 mg.

59. The method of clause 1, any other suitable clause, or any combination of suitable clauses, wherein the pharmaceutical composition comprises a compound present at a dose of 400 mg.

60. The method of clause 1, any other suitable clause, or any combination of suitable clauses, wherein the pharmaceutical composition comprises a compound present at a dose of 500 mg.

61. The method of clause 1, any other suitable clause, or any combination of suitable clauses, wherein the pharmaceutical composition comprises a compound present at a dose of 600 mg.

62. The method of clause 1, any other suitable clause, or any combination of suitable clauses, wherein the pharmaceutical composition comprises a compound present at a dose between 0.001 to 1000 mg of the compound per kg of patient body weight.

63. The method of clause 1, any other suitable clause, or any combination of suitable clauses, wherein the pharmaceutical composition comprises a compound present at a dose between 0.001 to 100 mg of the compound per kg of patient body weight.

64. The method of clause 1, any other suitable clause, or any combination of suitable clauses, wherein the pharmaceutical composition comprises a compound present at a dose between 0.01 to 100 mg of the compound per kg of patient body weight.

65. The method of clause 1, any other suitable clause, or any combination of suitable clauses, wherein the pharmaceutical composition comprises a compound present at a dose between 0.1 to 100 mg of the compound per kg of patient body weight.

66. The method of clause 1, any other suitable clause, or any combination of suitable clauses, wherein the pharmaceutical composition comprises a compound present at a dose between 0.1 to 10 mg of the compound per kg of patient body weight.

67. The method of clause 1, any other suitable clause, or any combination of suitable clauses, wherein the pharmaceutical composition comprises a compound present at a dose between 1 to 5 mg of the compound per kg of patient body weight.

68. The method of clause 1, any other suitable clause, or any combination of suitable clauses, wherein the pharmaceutical composition comprises a compound present at a dose of 2 mg of the compound per kg of patient body weight.

69. The method of clause 1, any other suitable clause, or any combination of suitable clauses, wherein the pharmaceutical composition comprises a compound present at a dose of 3 mg of the compound per kg of patient body weight.

70. The method of clause 1, any other suitable clause, or any combination of suitable clauses, wherein the pharmaceutical composition comprises a compound present at a dose of 4 mg of the compound per kg of patient body weight.

71. The method of clause 1, any other suitable clause, or any combination of suitable clauses, wherein the pharmaceutical composition comprises a compound present at a dose of 5 mg of the compound per kg of patient body weight.

72. The method of clause 1, any other suitable clause, or any combination of suitable clauses, wherein the method further comprises administration of a second therapeutic agent to the patient.

73. A method of treating COVID-19 in a patient in need thereof, said method comprising the step of administering a pharmaceutical composition to the patient, wherein the pharmaceutical composition provides inhibition of severe acute respiratory syndrome-coronavirus 2 (SARS-CoV-2) main protease ($M^{Pro}$) and wherein the pharmaceutical composition provides an increase in endosomal pH in one or more cells of the patient.

74. The method of clause 73, any other suitable clause, or any combination of suitable clauses, wherein COVID-19 is caused by infection with SARS-CoV-2.

75. The method of clause 73, any other suitable clause, or any combination of suitable clauses, wherein COVID-19 is caused by infection with a mutation of SARS-CoV-2.

76. The method of clause 73, any other suitable clause, or any combination of suitable clauses, wherein the patient is a human patient.

77. The method of clause 73, any other suitable clause, or any combination of suitable clauses, wherein the patient has severe COVID-19-related symptoms.

78. The method of clause 73, any other suitable clause, or any combination of suitable clauses, wherein the patient has mild COVID-19-related symptoms.

79. The method of clause 73, any other suitable clause, or any combination of suitable clauses, wherein the patient is asymptomatic for COVID-19-related symptoms but has been infected with SARS-CoV-2.

80. The method of clause 73, any other suitable clause, or any combination of suitable clauses, wherein the patient is at high risk for infection with SARS-CoV-2.

81. The method of clause 73, any other suitable clause, or any combination of suitable clauses, wherein the treatment is a prophylactic treatment of the patient prior to infection with SARS-CoV-2.

82. The method of clause 73, any other suitable clause, or any combination of suitable clauses, wherein the administration is an oral administration.

83. The method of clause 73, any other suitable clause, or any combination of suitable clauses, wherein the administration is a parenteral administration.

84. The method of clause 73, any other suitable clause, or any combination of suitable clauses, wherein the pharmaceutical composition comprises a compound with a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol.

85. The method of clause 73, any other suitable clause, or any combination of suitable clauses, wherein the pharmaceutical composition comprises a compound with a binding energy to $M^{Pro}$ at a value of less than −8.0 cal/mol.

86. The method of clause 73, any other suitable clause, or any combination of suitable clauses, wherein the pharmaceutical composition comprises a compound with a binding energy to $M^{Pro}$ at a value of less than −8.3 cal/mol.

87. The method of clause 73, any other suitable clause, or any combination of suitable clauses, wherein the pharmaceutical composition comprises a compound with a binding energy to $M^{Pro}$ at a value of less than −8.5 cal/mol.

88. The method of clause 73, any other suitable clause, or any combination of suitable clauses, wherein the pharmaceutical composition comprises a compound with a binding energy to $M^{Pro}$ at a value of less than −9.0 cal/mol.

89. The method of clause 73, any other suitable clause, or any combination of suitable clauses, wherein the pharmaceutical composition comprises a compound with a binding energy to $M^{Pro}$ at a value of less than −9.5 cal/mol.

90. The method of clause 73, any other suitable clause, or any combination of suitable clauses, wherein the pharmaceutical composition comprises a compound with a binding energy to $M^{Pro}$ at a value of less than −10.0 cal/mol.

91. The method of clause 73, any other suitable clause, or any combination of suitable clauses, wherein the pharmaceutical composition comprises a compound with an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

92. The method of clause 73, any other suitable clause, or any combination of suitable clauses, wherein the pharmaceutical composition comprises a compound with an $IC_{50}$ value for inhibition of $M^{Pro}$ of less than 100 μM.

93. The method of clause 73, any other suitable clause, or any combination of suitable clauses, wherein the pharmaceutical composition comprises a compound with an $IC_{50}$ value for inhibition of $M^{Pro}$) of less than 80 μM.

94. The method of clause 73, any other suitable clause, or any combination of suitable clauses, wherein the pharmaceutical composition comprises a compound with an $IC_{50}$ value for inhibition of $M^{Pro}$) of less than 70 μM.

95. The method of clause 73, any other suitable clause, or any combination of suitable clauses, wherein the pharmaceutical composition comprises a compound with an $IC_{50}$ value for inhibition of $M^{Pro}$) of less than 60 μM.

96. The method of clause 73, any other suitable clause, or any combination of suitable clauses, wherein the pharmaceutical composition comprises a compound with an $IC_{50}$ value for inhibition of $M^{Pro}$) of less than 50 μM.

97. The method of clause 73, any other suitable clause, or any combination of suitable clauses, wherein the pharmaceutical composition comprises a compound with an $IC_{50}$ value for inhibition of $M^{Pro}$) of less than 40 μM.

98. The method of clause 73, any other suitable clause, or any combination of suitable clauses, wherein the pharmaceutical composition comprises a compound providing inhibition of SARS-CoV-2-induced cytopathogenic effect (CPE).

99. The method of clause 98, any other suitable clause, or any combination of suitable clauses, wherein the inhibition of SARS-CoV-2-induced CPE is dose dependent.

100. The method of clause 98, any other suitable clause, or any combination of suitable clauses, wherein the inhibition of SARS-CoV-2-induced CPE is about 100%.

101. The method of clause 73, any other suitable clause, or any combination of suitable clauses, wherein the pharmaceutical composition comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

102. The method of clause 73, any other suitable clause, or any combination of suitable clauses, wherein the pharmaceutical composition comprises a compound selected from the group consisting of pimozide, ebastine, rupintrivir, bepridil, sertaconazole, rimonabant, and oxiconazole.

103. The method of clause 73, any other suitable clause, or any combination of suitable clauses, wherein the pharmaceutical composition comprises a compound selected from the group consisting of pimozide, ebastine, and bepridil.

104. The method of clause 73, any other suitable clause, or any combination of suitable clauses, wherein the pharmaceutical composition comprises a compound that is bepridil.

105. The method of clause 73, any other suitable clause, or any combination of suitable clauses, wherein the pharmaceutical composition comprises a compound that is pimozide.

106. The method of clause 73, any other suitable clause, or any combination of suitable clauses, wherein the pharmaceutical composition comprises a compound that is ebastine.

107. The method of clause 73, any other suitable clause, or any combination of suitable clauses, wherein the pharmaceutical composition comprises a compound that is rupintrivir.

108. The method of clause 73, any other suitable clause, or any combination of suitable clauses, wherein the pharmaceutical composition comprises a compound that is sertaconazole.

109. The method of clause 73, any other suitable clause, or any combination of suitable clauses, wherein the pharmaceutical composition comprises a compound that is rimonabant.

110. The method of clause 73, any other suitable clause, or any combination of suitable clauses, wherein the pharmaceutical composition comprises a compound that is oxiconazole.

111. The method of clause 73, any other suitable clause, or any combination of suitable clauses, wherein the pharmaceutical composition comprises a compound that is itraconazole.

112. The method of clause 73, any other suitable clause, or any combination of suitable clauses, wherein the pharmaceutical composition comprises a compound that is tipranavir.

113. The method of clause 73, any other suitable clause, or any combination of suitable clauses, wherein the pharmaceutical composition comprises a compound that is nelfinavir.

114. The method of clause 73, any other suitable clause, or any combination of suitable clauses, wherein the pharmaceutical composition comprises a compound that is zopiclone.

115. The method of clause 73, any other suitable clause, or any combination of suitable clauses, wherein the pharmaceutical composition comprises a compound that is trihexyphenidyl.

116. The method of clause 73, any other suitable clause, or any combination of suitable clauses, wherein the pharmaceutical composition comprises a compound that is saquinavir.

117. The method of clause 73, any other suitable clause, or any combination of suitable clauses, wherein the pharmaceutical composition comprises a compound that is isavuconazole.

118. The method of clause 73, any other suitable clause, or any combination of suitable clauses, wherein the pharmaceutical composition comprises a compound that is lopinavir.

119. The method of clause 73, any other suitable clause, or any combination of suitable clauses, wherein the pharmaceutical composition comprises a compound that is clemastine.

120. The method of clause 73, any other suitable clause, or any combination of suitable clauses, wherein the pharmaceutical composition comprises a compound that is metixene.

121. The method of clause 73, any other suitable clause, or any combination of suitable clauses, wherein the pharmaceutical composition comprises a compound that is duloxetine.

122. The method of clause 73, any other suitable clause, or any combination of suitable clauses, wherein the pharmaceutical composition comprises a compound present at a dose between 0.001 to 2000 mg.

123. The method of clause 73, any other suitable clause, or any combination of suitable clauses, wherein the pharmaceutical composition comprises a compound present at a dose between 1 to 2000 mg.

124. The method of clause 73, any other suitable clause, or any combination of suitable clauses, wherein the pharmaceutical composition comprises a compound present at a dose between 5 to 1500 mg.

125. The method of clause 73, any other suitable clause, or any combination of suitable clauses, wherein the pharmaceutical composition comprises a compound present at a dose between 10 to 1000 mg.

126. The method of clause 73, any other suitable clause, or any combination of suitable clauses, wherein the pharmaceutical composition comprises a compound present at a dose between 100 to 800 mg.

127. The method of clause 73, any other suitable clause, or any combination of suitable clauses, wherein the pharmaceutical composition comprises a compound present at a dose between 200 to 600 mg.

128. The method of clause 73, any other suitable clause, or any combination of suitable clauses, wherein the pharmaceutical composition comprises a compound present at a dose of 200 mg.

129. The method of clause 73, any other suitable clause, or any combination of suitable clauses, wherein the pharmaceutical composition comprises a compound present at a dose of 300 mg.

130. The method of clause 73, any other suitable clause, or any combination of suitable clauses, wherein the pharmaceutical composition comprises a compound present at a dose of 400 mg.

131. The method of clause 73, any other suitable clause, or any combination of suitable clauses, wherein the pharmaceutical composition comprises a compound present at a dose of 500 mg.

132. The method of clause 73, any other suitable clause, or any combination of suitable clauses, wherein the pharmaceutical composition comprises a compound present at a dose of 600 mg.

133. The method of clause 73, any other suitable clause, or any combination of suitable clauses, wherein the pharmaceutical composition comprises a compound present at a dose between 0.001 to 1000 mg of the compound per kg of patient body weight.

134. The method of clause 73, any other suitable clause, or any combination of suitable clauses, wherein the pharmaceutical composition comprises a compound present at a dose between 0.001 to 100 mg of the compound per kg of patient body weight.

135. The method of clause 73, any other suitable clause, or any combination of suitable clauses, wherein the pharmaceutical composition comprises a compound present at a dose between 0.01 to 100 mg of the compound per kg of patient body weight.

136. The method of clause 73, any other suitable clause, or any combination of suitable clauses, wherein the pharmaceutical composition comprises a compound present at a dose between 0.1 to 100 mg of the compound per kg of patient body weight.

137. The method of clause 73, any other suitable clause, or any combination of suitable clauses, wherein the pharmaceutical composition comprises a compound present at a dose between 0.1 to 10 mg of the compound per kg of patient body weight.

138. The method of clause 73, any other suitable clause, or any combination of suitable clauses, wherein the pharmaceutical composition comprises a compound present at a dose between 1 to 5 mg of the compound per kg of patient body weight.

139. The method of clause 73, any other suitable clause, or any combination of suitable clauses, wherein the pharmaceutical composition comprises a compound present at a dose of 2 mg of the compound per kg of patient body weight.

140. The method of clause 73, any other suitable clause, or any combination of suitable clauses, wherein the pharmaceutical composition comprises a compound present at a dose of 3 mg of the compound per kg of patient body weight.

141. The method of clause 73, any other suitable clause, or any combination of suitable clauses, wherein the pharmaceutical composition comprises a compound present at a dose of 4 mg of the compound per kg of patient body weight.

142. The method of clause 73, any other suitable clause, or any combination of suitable clauses, wherein the pharmaceutical composition comprises a compound present at a dose of 5 mg of the compound per kg of patient body weight.

143. The method of clause 73, any other suitable clause, or any combination of suitable clauses, wherein the method further comprises administration of a second therapeutic agent to the patient.

144. A method of inhibiting severe acute respiratory syndrome-coronavirus 2 (SARS-CoV-2) main protease ($M^{Pro}$) in a patient infected with SARS-CoV-2, said method comprising the step of administering a pharmaceutical composition to the patient, wherein the pharmaceutical composition provides inhibition of SARS-CoV-2 $M^{Pro}$.

145. The method of clause 144, any other suitable clause, or any combination of suitable clauses, wherein SARS-CoV-2 infection is caused by infection with a mutation of SARS-CoV-2.

146. The method of clause 144, any other suitable clause, or any combination of suitable clauses, wherein COVID-19 is caused by infection with a mutation of SARS-CoV-2.

147. The method of clause 144, any other suitable clause, or any combination of suitable clauses, wherein the patient is a human patient.

148. The method of clause 144, any other suitable clause, or any combination of suitable clauses, wherein the patient has severe COVID-19-related symptoms.

149. The method of clause 144, any other suitable clause, or any combination of suitable clauses, wherein the patient has mild COVID-19-related symptoms.

150. The method of clause 144, any other suitable clause, or any combination of suitable clauses, wherein the patient is asymptomatic for COVID-19-related symptoms but has been infected with SARS-CoV-2.

151. The method of clause 144, any other suitable clause, or any combination of suitable clauses, wherein the patient is at high risk for infection with SARS-CoV-2.

152. The method of clause 144, any other suitable clause, or any combination of suitable clauses, wherein the treatment is a prophylactic treatment of the patient prior to infection with SARS-CoV-2.

153. The method of clause 144, any other suitable clause, or any combination of suitable clauses, wherein the pharmaceutical composition provides an increase in endosomal pH in one or more cells of the patient.

154. The method of clause 144, any other suitable clause, or any combination of suitable clauses, wherein the administration is an oral administration.

155. The method of clause 144, any other suitable clause, or any combination of suitable clauses, wherein the administration is a parenteral administration.

156. The method of clause 144, any other suitable clause, or any combination of suitable clauses, wherein the pharmaceutical composition comprises a compound with a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol.

157. The method of clause 144, any other suitable clause, or any combination of suitable clauses, wherein the pharmaceutical composition comprises a compound with a binding energy to $M^{Pro}$ at a value of less than −8.0 cal/mol.

158. The method of clause 144, any other suitable clause, or any combination of suitable clauses, wherein the pharmaceutical composition comprises a compound with a binding energy to $M^{Pro}$ at a value of less than −8.3 cal/mol.

159. The method of clause 144, any other suitable clause, or any combination of suitable clauses, wherein the pharmaceutical composition comprises a compound with a binding energy to $M^{Pro}$ at a value of less than −8.5 cal/mol.

160. The method of clause 144, any other suitable clause, or any combination of suitable clauses, wherein the pharmaceutical composition comprises a compound with a binding energy to $M^{Pro}$ at a value of less than −9.0 cal/mol.

161. The method of clause 144, any other suitable clause, or any combination of suitable clauses, wherein the pharmaceutical composition comprises a compound with a binding energy to $M^{Pro}$ at a value of less than −9.5 cal/mol.

162. The method of clause 144, any other suitable clause, or any combination of suitable clauses, wherein the pharmaceutical composition comprises a compound with a binding energy to $M^{Pro}$ at a value of less than −10.0 cal/mol.

163. The method of clause 144, any other suitable clause, or any combination of suitable clauses, wherein the pharmaceutical composition comprises a compound with an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

164. The method of clause 144, any other suitable clause, or any combination of suitable clauses, wherein the pharmaceutical composition comprises a compound with an $IC_{50}$ value for inhibition of $M^{Pro}$ of less than 100 μM.

165. The method of clause 144, any other suitable clause, or any combination of suitable clauses, wherein the pharmaceutical composition comprises a compound with an $IC_{50}$ value for inhibition of $M^{Pro}$ of less than 80 μM.

166. The method of clause 144, any other suitable clause, or any combination of suitable clauses, wherein the pharmaceutical composition comprises a compound with an $IC_{50}$ value for inhibition of $M^{Pro}$ of less than 70 μM.

167. The method of clause 144, any other suitable clause, or any combination of suitable clauses, wherein the pharmaceutical composition comprises a compound with an $IC_{50}$ value for inhibition of $M^{Pro}$ of less than 60 μM.

168. The method of clause 144, any other suitable clause, or any combination of suitable clauses, wherein the pharmaceutical composition comprises a compound with an $IC_{50}$ value for inhibition of $M^{Pro}$ of less than 50 μM.

169. The method of clause 144, any other suitable clause, or any combination of suitable clauses, wherein the pharmaceutical composition comprises a compound with an $IC_{50}$ value for inhibition of $M^{Pro}$ of less than 40 μM.

170. The method of clause 144, any other suitable clause, or any combination of suitable clauses, wherein the pharmaceutical composition comprises a compound providing inhibition of SARS-CoV-2-induced cytopathogenic effect (CPE).

171. The method of clause 170, any other suitable clause, or any combination of suitable clauses, wherein the inhibition of SARS-CoV-2-induced CPE is dose dependent.

172. The method of clause 170, any other suitable clause, or any combination of suitable clauses, wherein the inhibition of SARS-CoV-2-induced CPE is about 100%.

173. The method of clause 144, any other suitable clause, or any combination of suitable clauses, wherein the pharmaceutical composition comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

174. The method of clause 144, any other suitable clause, or any combination of suitable clauses, wherein the pharmaceutical composition comprises a compound selected from the group consisting of pimozide, ebastine, rupintrivir, bepridil, sertaconazole, rimonabant, and oxiconazole.

175. The method of clause 144, any other suitable clause, or any combination of suitable clauses, wherein the pharmaceutical composition comprises a compound selected from the group consisting of pimozide, ebastine, and bepridil.

176. The method of clause 144, any other suitable clause, or any combination of suitable clauses, wherein the pharmaceutical composition comprises a compound that is bepridil.

177. The method of clause 144, any other suitable clause, or any combination of suitable clauses, wherein the pharmaceutical composition comprises a compound that is pimozide.

178. The method of clause 144, any other suitable clause, or any combination of suitable clauses, wherein the pharmaceutical composition comprises a compound that is ebastine.

179. The method of clause 144, any other suitable clause, or any combination of suitable clauses, wherein the pharmaceutical composition comprises a compound that is rupintrivir.

180. The method of clause 144, any other suitable clause, or any combination of suitable clauses, wherein the pharmaceutical composition comprises a compound that is sertaconazole.

181. The method of clause 144, any other suitable clause, or any combination of suitable clauses, wherein the pharmaceutical composition comprises a compound that is rimonabant.

182. The method of clause 144, any other suitable clause, or any combination of suitable clauses, wherein the pharmaceutical composition comprises a compound that is oxiconazole.

183. The method of clause 144, any other suitable clause, or any combination of suitable clauses, wherein the pharmaceutical composition comprises a compound that is itraconazole.

184. The method of clause 144, any other suitable clause, or any combination of suitable clauses, wherein the pharmaceutical composition comprises a compound that is tipranavir.

185. The method of clause 144, any other suitable clause, or any combination of suitable clauses, wherein the pharmaceutical composition comprises a compound that is nelfinavir.

186. The method of clause 144, any other suitable clause, or any combination of suitable clauses, wherein the pharmaceutical composition comprises a compound that is zopiclone.

187. The method of clause 144, any other suitable clause, or any combination of suitable clauses, wherein the pharmaceutical composition comprises a compound that is trihexyphenidyl.

188. The method of clause 144, any other suitable clause, or any combination of suitable clauses, wherein the pharmaceutical composition comprises a compound that is saquinavir.

189. The method of clause 144, any other suitable clause, or any combination of suitable clauses, wherein the pharmaceutical composition comprises a compound that is isavuconazole.

190. The method of clause 144, any other suitable clause, or any combination of suitable clauses, wherein the pharmaceutical composition comprises a compound that is lopinavir.

191. The method of clause 144, any other suitable clause, or any combination of suitable clauses, wherein the pharmaceutical composition comprises a compound that is clemastine.

192. The method of clause 144, any other suitable clause, or any combination of suitable clauses, wherein the pharmaceutical composition comprises a compound that is metixene.

193. The method of clause 144, any other suitable clause, or any combination of suitable clauses, wherein the pharmaceutical composition comprises a compound that is duloxetine.

194. The method of clause 144, any other suitable clause, or any combination of suitable clauses, wherein the pharmaceutical composition comprises a compound present at a dose between 0.001 to 2000 mg.

195. The method of clause 144, any other suitable clause, or any combination of suitable clauses, wherein the pharmaceutical composition comprises a compound present at a dose between 1 to 2000 mg.

196. The method of clause 144, any other suitable clause, or any combination of suitable clauses, wherein the pharmaceutical composition comprises a compound present at a dose between 5 to 1500 mg.

197. The method of clause 144, any other suitable clause, or any combination of suitable clauses, wherein the pharmaceutical composition comprises a compound present at a dose between 10 to 1000 mg.

198. The method of clause 144, any other suitable clause, or any combination of suitable clauses, wherein the pharmaceutical composition comprises a compound present at a dose between 100 to 800 mg.

199. The method of clause 144, any other suitable clause, or any combination of suitable clauses, wherein the pharmaceutical composition comprises a compound present at a dose between 200 to 600 mg.

200. The method of clause 144, any other suitable clause, or any combination of suitable clauses, wherein the pharmaceutical composition comprises a compound present at a dose of 200 mg.

201. The method of clause 144, any other suitable clause, or any combination of suitable clauses, wherein the pharmaceutical composition comprises a compound present at a dose of 300 mg.

202. The method of clause 144, any other suitable clause, or any combination of suitable clauses, wherein the pharmaceutical composition comprises a compound present at a dose of 400 mg.

203. The method of clause 144, any other suitable clause, or any combination of suitable clauses, wherein the pharmaceutical composition comprises a compound present at a dose of 500 mg.

204. The method of clause 144, any other suitable clause, or any combination of suitable clauses, wherein the pharmaceutical composition comprises a compound present at a dose of 600 mg.

205. The method of clause 144, any other suitable clause, or any combination of suitable clauses, wherein the pharmaceutical composition comprises a compound present at a dose between 0.001 to 1000 mg of the compound per kg of patient body weight.

206. The method of clause 144, any other suitable clause, or any combination of suitable clauses, wherein the pharmaceutical composition comprises a compound present at a dose between 0.001 to 100 mg of the compound per kg of patient body weight.

207. The method of clause 144, any other suitable clause, or any combination of suitable clauses, wherein the pharmaceutical composition comprises a compound present at a dose between 0.01 to 100 mg of the compound per kg of patient body weight.

208. The method of clause 144, any other suitable clause, or any combination of suitable clauses, wherein the pharmaceutical composition comprises a compound present at a dose between 0.1 to 100 mg of the compound per kg of patient body weight.

209. The method of clause 144, any other suitable clause, or any combination of suitable clauses, wherein the pharmaceutical composition comprises a compound present at a dose between 0.1 to 10 mg of the compound per kg of patient body weight.

210. The method of clause 144, any other suitable clause, or any combination of suitable clauses, wherein the pharmaceutical composition comprises a compound present at a dose between 1 to 5 mg of the compound per kg of patient body weight.

211. The method of clause 144, any other suitable clause, or any combination of suitable clauses, wherein the pharmaceutical composition comprises a compound present at a dose of 2 mg of the compound per kg of patient body weight.

212. The method of clause 144, any other suitable clause, or any combination of suitable clauses, wherein the pharmaceutical composition comprises a compound present at a dose of 3 mg of the compound per kg of patient body weight.

213. The method of clause 144, any other suitable clause, or any combination of suitable clauses, wherein the pharmaceutical composition comprises a compound present at a dose of 4 mg of the compound per kg of patient body weight.

214. The method of clause 144, any other suitable clause, or any combination of suitable clauses, wherein the pharmaceutical composition comprises a compound present at a dose of 5 mg of the compound per kg of patient body weight.

215. The method of clause 144, any other suitable clause, or any combination of suitable clauses, wherein the method further comprises administration of a second therapeutic agent to the patient.

216. A method of treating a coronavirus infection in a patient, said method comprising the step of administering a pharmaceutical composition to the patient.

217. The method of clause 216, any other suitable clause, or any combination of suitable clauses, wherein the coronavirus infection is an infection caused by SARS-CoV-2.

218. The method of clause 216, any other suitable clause, or any combination of suitable clauses, wherein the coronavirus infection is an infection caused by a SARS-CoV-2 mutation.

219. The method of clause 216, any other suitable clause, or any combination of suitable clauses, wherein the pharmaceutical composition provides inhibition of SARS-CoV-2 $M^{Pro}$.

220. The method of clause 216, any other suitable clause, or any combination of suitable clauses, wherein the pharmaceutical composition provides an increase in endosomal pH in one or more cells of the patient.

221. The method of clause 216, any other suitable clause, or any combination of suitable clauses, wherein the pharmaceutical composition provides inhibition of SARS-CoV-2 $M^{Pro}$ and wherein the pharmaceutical composition provides an increase in endosomal pH in one or more cells of the patient.

222. The method of clause 216, any other suitable clause, or any combination of suitable clauses, wherein the patient is a human patient.

223. The method of clause 216, any other suitable clause, or any combination of suitable clauses, wherein the patient has severe coronavirus-related symptoms.

224. The method of clause 216, any other suitable clause, or any combination of suitable clauses, wherein the patient has mild coronavirus-related symptoms.

225. The method of clause 216, any other suitable clause, or any combination of suitable clauses, wherein the patient is asymptomatic for coronavirus-related symptoms but has been infected with coronavirus.

226. The method of clause 216, any other suitable clause, or any combination of suitable clauses, wherein the patient is at high risk for infection with coronavirus.

227. The method of clause 216, any other suitable clause, or any combination of suitable clauses, wherein the treatment is a prophylactic treatment of the patient prior to infection with coronavirus.

228. The method of clause 216, any other suitable clause, or any combination of suitable clauses, wherein the administration is an oral administration.

229. The method of clause 216, any other suitable clause, or any combination of suitable clauses, wherein the administration is a parenteral administration.

230. The method of clause 216, any other suitable clause, or any combination of suitable clauses, wherein the pharmaceutical composition comprises a compound with a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol.

231. The method of clause 216, any other suitable clause, or any combination of suitable clauses, wherein the pharmaceutical composition comprises a compound with a binding energy to $M^{Pro}$ at a value of less than −8.0 cal/mol.

232. The method of clause 216, any other suitable clause, or any combination of suitable clauses, wherein the pharmaceutical composition comprises a compound with a binding energy to $M^{Pro}$ at a value of less than −8.3 cal/mol.

233. The method of clause 216, any other suitable clause, or any combination of suitable clauses, wherein the pharmaceutical composition comprises a compound with a binding energy to $M^{Pro}$ at a value of less than −8.5 cal/mol.

234. The method of clause 216, any other suitable clause, or any combination of suitable clauses, wherein the pharmaceutical composition comprises a compound with a binding energy to $M^{Pro}$ at a value of less than −9.0 cal/mol.

235. The method of clause 216, any other suitable clause, or any combination of suitable clauses, wherein the pharmaceutical composition comprises a compound with a binding energy to $M^{Pro}$ at a value of less than −9.5 cal/mol.

236. The method of clause 216, any other suitable clause, or any combination of suitable clauses, wherein the pharmaceutical composition comprises a compound with a binding energy to $M^{Pro}$ at a value of less than −10.0 cal/mol.

237. The method of clause 216, any other suitable clause, or any combination of suitable clauses, wherein the pharmaceutical composition comprises a compound with an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

238. The method of clause 216, any other suitable clause, or any combination of suitable clauses, wherein the pharmaceutical composition comprises a compound with an $IC_{50}$ value for inhibition of $M^{Pro}$ of less than 100 μM.

239. The method of clause 216, any other suitable clause, or any combination of suitable clauses, wherein the pharmaceutical composition comprises a compound with an $IC_{50}$ value for inhibition of $M^{Pro}$ of less than 80 μM.

240. The method of clause 216, any other suitable clause, or any combination of suitable clauses, wherein the pharmaceutical composition comprises a compound with an $IC_{50}$ value for inhibition of $M^{Pro}$ of less than 70 µM.

241. The method of clause 216, any other suitable clause, or any combination of suitable clauses, wherein the pharmaceutical composition comprises a compound with an $IC_{50}$ value for inhibition of $M^{Pro}$ of less than 60 µM.

242. The method of clause 216, any other suitable clause, or any combination of suitable clauses, wherein the pharmaceutical composition comprises a compound with an $IC_{50}$ value for inhibition of $M^{Pro}$) of less than 50 µM.

243. The method of clause 216, any other suitable clause, or any combination of suitable clauses, wherein the pharmaceutical composition comprises a compound with an $IC_{50}$ value for inhibition of $M^{Pro}$) of less than 40 µM.

244. The method of clause 216, any other suitable clause, or any combination of suitable clauses, wherein the pharmaceutical composition comprises a compound providing inhibition of SARS-CoV-2-induced cytopathogenic effect (CPE).

245. The method of clause 244, any other suitable clause, or any combination of suitable clauses, wherein the inhibition of SARS-CoV-2-induced CPE is dose dependent.

246. The method of clause 244, any other suitable clause, or any combination of suitable clauses, wherein the inhibition of SARS-CoV-2-induced CPE is about 100%.

247. The method of clause 216, any other suitable clause, or any combination of suitable clauses, wherein the pharmaceutical composition comprises a compound selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

248. The method of clause 216, any other suitable clause, or any combination of suitable clauses, wherein the pharmaceutical composition comprises a compound selected from the group consisting of pimozide, ebastine, rupintrivir, bepridil, sertaconazole, rimonabant, and oxiconazole.

249. The method of clause 216, any other suitable clause, or any combination of suitable clauses, wherein the pharmaceutical composition comprises a compound selected from the group consisting of pimozide, ebastine, and bepridil.

250. The method of clause 216, any other suitable clause, or any combination of suitable clauses, wherein the pharmaceutical composition comprises a compound that is bepridil.

251. The method of clause 216, any other suitable clause, or any combination of suitable clauses, wherein the pharmaceutical composition comprises a compound that is pimozide.

252. The method of clause 216, any other suitable clause, or any combination of suitable clauses, wherein the pharmaceutical composition comprises a compound that is ebastine.

253. The method of clause 216, any other suitable clause, or any combination of suitable clauses, wherein the pharmaceutical composition comprises a compound that is rupintrivir.

254. The method of clause 216, any other suitable clause, or any combination of suitable clauses, wherein the pharmaceutical composition comprises a compound that is sertaconazole.

255. The method of clause 216, any other suitable clause, or any combination of suitable clauses, wherein the pharmaceutical composition comprises a compound that is rimonabant.

256. The method of clause 216, any other suitable clause, or any combination of suitable clauses, wherein the pharmaceutical composition comprises a compound that is oxiconazole.

257. The method of clause 216, any other suitable clause, or any combination of suitable clauses, wherein the pharmaceutical composition comprises a compound that is itraconazole.

258. The method of clause 216, any other suitable clause, or any combination of suitable clauses, wherein the pharmaceutical composition comprises a compound that is tipranavir.

259. The method of clause 216, any other suitable clause, or any combination of suitable clauses, wherein the pharmaceutical composition comprises a compound that is nelfinavir.

260. The method of clause 216, any other suitable clause, or any combination of suitable clauses, wherein the pharmaceutical composition comprises a compound that is zopiclone.

261. The method of clause 216, any other suitable clause, or any combination of suitable clauses, wherein the pharmaceutical composition comprises a compound that is trihexyphenidyl.

262. The method of clause 216, any other suitable clause, or any combination of suitable clauses, wherein the pharmaceutical composition comprises a compound that is saquinavir.

263. The method of clause 216, any other suitable clause, or any combination of suitable clauses, wherein the pharmaceutical composition comprises a compound that is isavuconazole.

264. The method of clause 216, any other suitable clause, or any combination of suitable clauses, wherein the pharmaceutical composition comprises a compound that is lopinavir.

265. The method of clause 216, any other suitable clause, or any combination of suitable clauses, wherein the pharmaceutical composition comprises a compound that is clemastine.

266. The method of clause 216, any other suitable clause, or any combination of suitable clauses, wherein the pharmaceutical composition comprises a compound that is metixene.

267. The method of clause 216, any other suitable clause, or any combination of suitable clauses, wherein the pharmaceutical composition comprises a compound that is duloxetine.

268. The method of clause 216, any other suitable clause, or any combination of suitable clauses, wherein the pharmaceutical composition comprises a compound present at a dose between 0.001 to 2000 mg.

269. The method of clause 216, any other suitable clause, or any combination of suitable clauses, wherein the pharmaceutical composition comprises a compound present at a dose between 1 to 2000 mg.

270. The method of clause 216, any other suitable clause, or any combination of suitable clauses, wherein the pharmaceutical composition comprises a compound present at a dose between 5 to 1500 mg.

271. The method of clause 216, any other suitable clause, or any combination of suitable clauses, wherein the pharmaceutical composition comprises a compound present at a dose between 10 to 1000 mg.

272. The method of clause 216, any other suitable clause, or any combination of suitable clauses, wherein the pharmaceutical composition comprises a compound present at a dose between 100 to 800 mg.

273. The method of clause 216, any other suitable clause, or any combination of suitable clauses, wherein the pharmaceutical composition comprises a compound present at a dose between 200 to 600 mg.

274. The method of clause 216, any other suitable clause, or any combination of suitable clauses, wherein the pharmaceutical composition comprises a compound present at a dose of 200 mg.

275. The method of clause 216, any other suitable clause, or any combination of suitable clauses, wherein the pharmaceutical composition comprises a compound present at a dose of 300 mg.

276. The method of clause 216, any other suitable clause, or any combination of suitable clauses, wherein the pharmaceutical composition comprises a compound present at a dose of 400 mg.

277. The method of clause 216, any other suitable clause, or any combination of suitable clauses, wherein the pharmaceutical composition comprises a compound present at a dose of 500 mg.

278. The method of clause 216, any other suitable clause, or any combination of suitable clauses, wherein the pharmaceutical composition comprises a compound present at a dose of 600 mg.

279. The method of clause 216, any other suitable clause, or any combination of suitable clauses, wherein the pharmaceutical composition comprises a compound present at a dose between 0.001 to 1000 mg of the compound per kg of patient body weight.

280. The method of clause 216, any other suitable clause, or any combination of suitable clauses, wherein the pharmaceutical composition comprises a compound present at a dose between 0.001 to 100 mg of the compound per kg of patient body weight.

281. The method of clause 216, any other suitable clause, or any combination of suitable clauses, wherein the pharmaceutical composition comprises a compound present at a dose between 0.01 to 100 mg of the compound per kg of patient body weight.

282. The method of clause 216, any other suitable clause, or any combination of suitable clauses, wherein the pharmaceutical composition comprises a compound present at a dose between 0.1 to 100 mg of the compound per kg of patient body weight.

283. The method of clause 216, any other suitable clause, or any combination of suitable clauses, wherein the pharmaceutical composition comprises a compound present at a dose between 0.1 to 10 mg of the compound per kg of patient body weight.

284. The method of clause 216, any other suitable clause, or any combination of suitable clauses, wherein the pharmaceutical composition comprises a compound present at a dose between 1 to 5 mg of the compound per kg of patient body weight.

285. The method of clause 216, any other suitable clause, or any combination of suitable clauses, wherein the pharmaceutical composition comprises a compound present at a dose of 2 mg of the compound per kg of patient body weight.

286. The method of clause 216, any other suitable clause, or any combination of suitable clauses, wherein the pharmaceutical composition comprises a compound present at a dose of 3 mg of the compound per kg of patient body weight.

287. The method of clause 216, any other suitable clause, or any combination of suitable clauses, wherein the phar-maceutical composition comprises a compound present at a dose of 4 mg of the compound per kg of patient body weight.

288. The method of clause 216, any other suitable clause, or any combination of suitable clauses, wherein the pharmaceutical composition comprises a compound present at a dose of 5 mg of the compound per kg of patient body weight.

289. The method of clause 216, any other suitable clause, or any combination of suitable clauses, wherein the method further comprises administration of a second therapeutic agent to the patient.

290. A pharmaceutical formulation for use in treating a COVID-19 patient, said pharmaceutical formulation comprising a therapeutically effective amount of a compound that inhibits severe acute respiratory syndrome-coronavirus 2 (SARS-CoV-2) main protease ($M^{Pro}$).

291. The pharmaceutical formulation of clause 290, any other suitable clause, or any combination of suitable clauses, wherein COVID-19 is caused by infection with SARS-CoV-2.

292. The pharmaceutical formulation of clause 290, any other suitable clause, or any combination of suitable clauses, wherein COVID-19 is caused by infection with a mutation of SARS-CoV-2.

293. The pharmaceutical formulation of clause 290, any other suitable clause, or any combination of suitable clauses, wherein the patient is a human patient.

294. The pharmaceutical formulation of clause 290, any other suitable clause, or any combination of suitable clauses, wherein the pharmaceutical formulation is adapted for treatment of a patient with severe COVID-19-related symptoms.

295. The pharmaceutical formulation of clause 290, any other suitable clause, or any combination of suitable clauses, wherein the pharmaceutical formulation is adapted for treatment of a patient with mild COVID-19-related symptoms.

296. The pharmaceutical formulation of clause 290, any other suitable clause, or any combination of suitable clauses, wherein the pharmaceutical formulation is adapted for treatment of a patient that is asymptomatic for coronavirus-related symptoms but has been infected with SARS-CoV-2.

297. The pharmaceutical formulation of clause 290, any other suitable clause, or any combination of suitable clauses, wherein the pharmaceutical formulation is adapted for treatment of a patient at high risk for infection with SARS-CoV-2.

298. The pharmaceutical formulation of clause 290, any other suitable clause, or any combination of suitable clauses, wherein the pharmaceutical formulation is adapted for treatment of a patient prior to infection with SARS-CoV-2.

299. The pharmaceutical formulation of clause 290, any other suitable clause, or any combination of suitable clauses, wherein the pharmaceutical formulation is an oral formulation.

300. The pharmaceutical formulation of clause 299, any other suitable clause, or any combination of suitable clauses, wherein the oral formulation is selected from the group consisting of tablets, capsules, hard or soft gelatin capsules, pellets, pills, powders, granules, elixirs, tinctures, colloidal dispersions, dispersions, effervescent compositions, films, sterile solutions, sterile suspensions, syrups, and emulsions.

301. The pharmaceutical formulation of clause 290, any other suitable clause, or any combination of suitable clauses, wherein the pharmaceutical formulation is a parenteral formulation.

302. The pharmaceutical formulation of clause 301, any other suitable clause, or any combination of suitable clauses, wherein the parenteral formulation is selected from the group consisting of intravenous, intraarterial, intraperito- 303. The pharmaceutical formulation of clause 290, any other suitable clause, or any combination of suitable clauses, wherein the compound has a binding energy to $M^{Pro}$ selected from the group consisting of a value of less than −8.0 cal/mol, a value of less than −8.3 cal/mol, a value of less than −8.5 cal/mol, a value of less than −9.0 cal/mol, a value of less than −9.5 cal/mol, and a value of less than −10.0 cal/mol.

304. The pharmaceutical formulation of clause 290, any other suitable clause, or any combination of suitable clauses, wherein the compound has a binding energy to $M^{Pro}$ at a value of less than −8.0 cal/mol.

305. The pharmaceutical formulation of clause 290, any other suitable clause, or any combination of suitable clauses, wherein the compound has a binding energy to $M^{Pro}$ at a value of less than −8.3 cal/mol.

306. The pharmaceutical formulation of clause 290, any other suitable clause, or any combination of suitable clauses, wherein the compound has a binding energy to $M^{Pro}$ at a value of less than −8.5 cal/mol.

307. The pharmaceutical formulation of clause 290, any other suitable clause, or any combination of suitable clauses, wherein the compound has a binding energy to $M^{Pro}$ at a value of less than −9.0 cal/mol.

308. The pharmaceutical formulation of clause 290, any other suitable clause, or any combination of suitable clauses, wherein the compound has a binding energy to $M^{Pro}$ at a value of less than −9.5 cal/mol.

309. The pharmaceutical formulation of clause 290, any other suitable clause, or any combination of suitable clauses, wherein the compound has a binding energy to $M^{Pro}$ at a value of less than −10.0 cal/mol.

310. The pharmaceutical formulation of clause 290, any other suitable clause, or any combination of suitable clauses, wherein the compound has an $IC_{50}$ value for inhibition of $M^{Pro}$ selected from the group consisting of less than 100 μM, less than 90 μM, less than 80 μM, less than 70 μM, less than 60 μM, less than 50 μM, and less than 40 μM.

311. The pharmaceutical formulation of clause 290, any other suitable clause, or any combination of suitable clauses, wherein the compound has an $IC_{50}$ value for inhibition of $M^{Pro}$ of less than 100 μM.

312. The pharmaceutical formulation of clause 290, any other suitable clause, or any combination of suitable clauses, wherein the compound has an $IC_{50}$ value for inhibition of $M^{Pro}$ of less than 80 μM.

313. The pharmaceutical formulation of clause 290, any other suitable clause, or any combination of suitable clauses, wherein the compound has an $IC_{50}$ value for inhibition of $M^{Pro}$ of less than 70 μM.

314. The pharmaceutical formulation of clause 290, any other suitable clause, or any combination of suitable clauses, wherein the compound has an $IC_{50}$ value for inhibition of $M^{Pro}$ of less than 60 μM.

315. The pharmaceutical formulation of clause 290, any other suitable clause, or any combination of suitable clauses, wherein the compound has an $IC_{50}$ value for inhibition of $M^{Pro}$ of less than 50 μM.

316. The pharmaceutical formulation of clause 290, any other suitable clause, or any combination of suitable clauses, wherein the compound has an $IC_{50}$ value for inhibition of $M^{Pro}$ of less than 40 μM.

317. The pharmaceutical formulation of clause 290, any other suitable clause, or any combination of suitable clauses, wherein the compound provides inhibition of SARS-CoV-2-induced cytopathogenic effect (CPE).

318. The pharmaceutical formulation of clause 317, any other suitable clause, or any combination of suitable clauses, wherein the inhibition of SARS-CoV-2-induced CPE is dose dependent.

319. The pharmaceutical formulation of clause 317, any other suitable clause, or any combination of suitable clauses, wherein the inhibition of SARS-CoV-2-induced CPE is about 100%.

320. The pharmaceutical formulation of clause 290, any other suitable clause, or any combination of suitable clauses, wherein the compound is selected from the group consisting of pimozide, ebastine, rupintrivir, bepridil, sertaconazole, rimonabant, oxiconazole, itraconazole, tipranavir, nelfinavir, zopiclone, trihexyphenidyl, saquinavir, isavuconazole, lopinavir, clemastine, metixene, and duloxetine.

321. The pharmaceutical formulation of clause 290, any other suitable clause, or any combination of suitable clauses, wherein the compound is selected from the group consisting of pimozide, ebastine, rupintrivir, bepridil, sertaconazole, rimonabant, and oxiconazole.

322. The pharmaceutical formulation of clause 290, any other suitable clause, or any combination of suitable clauses, wherein the compound is selected from the group consisting of pimozide, ebastine, and bepridil.

323. The pharmaceutical formulation of clause 290, any other suitable clause, or any combination of suitable clauses, wherein the compound is bepridil.

324. The pharmaceutical formulation of clause 290, any other suitable clause, or any combination of suitable clauses, wherein the compound is pimozide.

325. The pharmaceutical formulation of clause 290, any other suitable clause, or any combination of suitable clauses, wherein the compound is ebastine.

326. The pharmaceutical formulation of clause 290, any other suitable clause, or any combination of suitable clauses, wherein the compound is rupintrivir.

327. The pharmaceutical formulation of clause 290, any other suitable clause, or any combination of suitable clauses, wherein the compound is sertaconazole.

328. The pharmaceutical formulation of clause 290, any other suitable clause, or any combination of suitable clauses, wherein the compound is rimonabant.

329. The pharmaceutical formulation of clause 290, any other suitable clause, or any combination of suitable clauses, wherein the compound is oxiconazole.

330. The pharmaceutical formulation of clause 290, any other suitable clause, or any combination of suitable clauses, wherein the compound is itraconazole.

331. The pharmaceutical formulation of clause 290, any other suitable clause, or any combination of suitable clauses, wherein the compound is tipranavir.

332. The pharmaceutical formulation of clause 290, any other suitable clause, or any combination of suitable clauses, wherein the compound is nelfinavir.

333. The pharmaceutical formulation of clause 290, any other suitable clause, or any combination of suitable clauses, wherein the compound is zopiclone.

334. The pharmaceutical formulation of clause 290, any other suitable clause, or any combination of suitable clauses, wherein the compound is trihexyphenidyl.

335. The pharmaceutical formulation of clause 290, any other suitable clause, or any combination of suitable clauses, wherein the compound is saquinavir.

336. The pharmaceutical formulation of clause 290, any other suitable clause, or any combination of suitable clauses, wherein the compound is isavuconazole.

337. The pharmaceutical formulation of clause 290, any other suitable clause, or any combination of suitable clauses, wherein the compound is lopinavir.

338. The pharmaceutical formulation of clause 290, any other suitable clause, or any combination of suitable clauses, wherein the compound is clemastine.

339. The pharmaceutical formulation of clause 290, any other suitable clause, or any combination of suitable clauses, wherein the compound is metixene.

340. The pharmaceutical formulation of clause 290, any other suitable clause, or any combination of suitable clauses, wherein the compound is duloxetine.

341. The pharmaceutical formulation of clause 290, any other suitable clause, or any combination of suitable clauses, wherein the compound is present at a dose between 0.001 to 2000 mg.

342. The pharmaceutical formulation of clause 290, any other suitable clause, or any combination of suitable clauses, wherein the compound is present at a dose between 1 to 2000 mg.

343. The pharmaceutical formulation of clause 290, any other suitable clause, or any combination of suitable clauses, wherein the compound is present at a dose between 5 to 1500 mg.

344. The pharmaceutical formulation of clause 290, any other suitable clause, or any combination of suitable clauses, wherein the compound is present at a dose between 10 to 1000 mg.

345. The pharmaceutical formulation of clause 290, any other suitable clause, or any combination of suitable clauses, wherein the compound is present at a dose between 100 to 800 mg.

346. The pharmaceutical formulation of clause 290, any other suitable clause, or any combination of suitable clauses, wherein the compound is present at a dose between 200 to 600 mg.

347. The pharmaceutical formulation of clause 290, any other suitable clause, or any combination of suitable clauses, wherein the compound is present at a dose of 200 mg.

348. The pharmaceutical formulation of clause 290, any other suitable clause, or any combination of suitable clauses, wherein the compound is present at a dose of 300 mg.

349. The pharmaceutical formulation of clause 290, any other suitable clause, or any combination of suitable clauses, wherein the compound is present at a dose of 400 mg.

350. The pharmaceutical formulation of clause 290, any other suitable clause, or any combination of suitable clauses, wherein the compound is present at a dose of 500 mg.

351. The pharmaceutical formulation of clause 290, any other suitable clause, or any combination of suitable clauses, wherein the compound is present at a dose of 600 mg.

352. The pharmaceutical formulation of clause 290, any other suitable clause, or any combination of suitable clauses, wherein the compound is present at a dose between 0.001 to 1000 mg of the compound per kg of patient body weight.

353. The pharmaceutical formulation of clause 290, any other suitable clause, or any combination of suitable clauses, wherein the compound is present at a dose between 0.001 to 100 mg of the compound per kg of patient body weight.

354. The pharmaceutical formulation of clause 290, any other suitable clause, or any combination of suitable clauses, wherein the compound is present at a dose between 0.01 to 100 mg of the compound per kg of patient body weight.

355. The pharmaceutical formulation of clause 290, any other suitable clause, or any combination of suitable clauses, wherein the compound is present at a dose between 0.1 to 100 mg of the compound per kg of patient body weight.

356. The pharmaceutical formulation of clause 290, any other suitable clause, or any combination of suitable clauses, wherein the compound is present at a dose between 0.1 to 10 mg of the compound per kg of patient body weight.

357. The pharmaceutical formulation of clause 290, any other suitable clause, or any combination of suitable clauses, wherein the compound is present at a dose between 1 to 5 mg of the compound per kg of patient body weight.

358. The pharmaceutical formulation of clause 290, any other suitable clause, or any combination of suitable clauses, wherein the compound is present at a dose of 2 mg of the compound per kg of patient body weight.

359. The pharmaceutical formulation of clause 290, any other suitable clause, or any combination of suitable clauses, wherein the compound is present at a dose of 3 mg of the compound per kg of patient body weight.

360. The pharmaceutical formulation of clause 290, any other suitable clause, or any combination of suitable clauses, wherein the compound is present at a dose of 4 mg of the compound per kg of patient body weight.

361. The pharmaceutical formulation of clause 290, any other suitable clause, or any combination of suitable clauses, wherein the compound is present at a dose of 5 mg of the compound per kg of patient body weight.

362. The pharmaceutical formulation of clause 290, any other suitable clause, or any combination of suitable clauses, wherein the pharmaceutical formulation is a unit dose.

363. The pharmaceutical formulation of clause 290, any other suitable clause, or any combination of suitable clauses, wherein the pharmaceutical formulation is a single unit dose.

364. The pharmaceutical formulation of clause 290, any other suitable clause, or any combination of suitable clauses, wherein the pharmaceutical formulation further comprises a second therapeutic agent.

365. The pharmaceutical formulation of clause 290, any other suitable clause, or any combination of suitable clauses, wherein the pharmaceutical formulation is adapted for administration with a second therapeutic agent.

366. The pharmaceutical formulation of clause 290, any other suitable clause, or any combination of suitable clauses, wherein the pharmaceutical formulation further comprises one or more pharmaceutically acceptable carriers.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Example 1

Docking Study of $M^{Pro}$ Structure Using Various Compositions

The first crystal structure of $M^{Pro}$ was released on Feb. 5, 2020 (Deng et al., "Structure of M(pro) from SARS-CoV-2 and discovery of its inhibitors," Nature; 10.1038/s41586-020-2223-y; incorporated herein by reference in its entirety). For the docking study of the instant example, this structure (the pdb entry 6lu7) was chosen.

$M^{Pro}$ has a very large active site that includes several smaller pockets for the recognition of amino acid residues in its protein substrates. It is believed that three pockets that bind the P1, P2, and P4 residues in a protein substrate potentially interact with aromatic and large hydrophobic moieties. Although the P1' residue in a protein substrate is a small residue such as glycine or serine, previous studies based on the functional enzyme from SARS-CoV-1 suggest that an aromatic moiety can occupy the site that originally bind the P1' and P2' residues in a substrate.

Based on the analysis of the $M^{Pro}$ structure, 55 different compositions (e.g., FDA/EMA-approved small molecules) were selected for analysis in the instant example. The selected compositions have several aromatic or large hydrophobic moieties inter-connected. A docking analysis of the binding of the 55 compositions to $M^{Pro}$ was performed.

Autodock 4 was adopted for the docking analysis of the instant example. The covalent ligand and non-bonded small molecules in the structure of 6lu7 were removed to prepare the protein structure for docking. Four residues (His41, Met49, Asn142, and Gln189) were set as flexible during the docking process. A genetic algorithm method with 100 runs was performed to dock each composition to the enzyme. For each composition, the genetic algorithm-based calculation was carried out for 100 runs with each run having a maximal number of evaluations as 2,500,000. The lowest binding energy from the total 100 runs was collected for each composition and results are summarized in Table 1.

TABLE 1

Docking results of evaluated compositions. Asterisks indicate compositions selected for evaluation of $IC_{50}$ values.

| Name | $\Delta G_{binding}$ (kcal/mol) |
|---|---|
| Rimonabant* | −11.23 |
| Tipranavir* | −10.74 |
| Ebastine* | −10.62 |
| Saquinavir* | −10.37 |
| Zopiclone* | −10.10 |
| Pimozide* | −10.01 |
| Pirenzepine* | −9.94 |
| Nelfinavir* | −9.67 |
| Doxapram* | −9.55 |
| Oxiconazole* | −9.18 |
| Indinavir* | −9.13 |
| Sertindole* | −9.04 |
| Metixene* | −9.01 |
| Fexofenadine* | −8.95 |
| Lopinavir* | −8.91 |
| Sertaconazole* | −8.87 |
| Reboxetine* | −8.86 |
| Ketoconazole* | −8.85 |
| Duloxetine* | −8.79 |
| Isavuconazole* | −8.77 |
| Lemborexant* | −8.75 |
| Oxyphencyclimine* | −8.74 |
| Darunavir* | −8.72 |
| Trihexphenidyl* | −8.72 |
| Pimavanserin* | −8.69 |
| Clotiapine* | −8.57 |
| Itraconazole* | −8.44 |
| Clemastine* | −8.36 |
| Bepridil* | −8.31 |
| Isoconazole | −8.15 |
| Econazole | −8.14 |
| Eluxadoline | −8.12 |
| (R)-Butoconazole | −8.11 |
| (S)-Butoconazole | −8.10 |

TABLE 1-continued

Docking results of evaluated compositions. Asterisks indicate compositions selected for evaluation of $IC_{50}$ values.

| Name | $\Delta G_{binding}$ (kcal/mol) |
|---|---|
| Atazanavir | −8.08 |
| Cetirizine | −8.01 |
| Efinaconazole | −8.01 |
| Amprenavir | −7.99 |
| Hydroxyzine | −7.99 |
| (R)-Tioconazole | −7.98 |
| (R)-Carbinoxamine | −7.96 |
| Armodafinil | −7.90 |
| Desipramine | −7.84 |
| Ritonavir | −7.74 |
| Atomoxetine | −7.73 |
| Sulconazole | −7.69 |
| Clotrimazole | −7.67 |
| Dipyridamole | −7.67 |
| Phentolamine | −7.61 |
| (S)-Tioconazole | −7.48 |
| Doxylamine | −7.33 |
| (S)-Carbinoxamine | −7.21 |
| Antazoline | −6.86 |
| Voriconazole | −6.76 |
| Fluconazole | −6.41 |

Among the 55 compositions evaluated in the instant example, 29 compositions demonstrated a binding energy lower than −8.3 kcal/mol. These 29 compositions were selected for further characterization.

Example 2

Preparation of $M^{Pro}$ and Assay Testing Conditions $M^{Pro}$ Expression and Purification The plasmid pBAD-sfGFP-$M^{Pro}$ was constructed from pBAD-sfGFP. The $M^{Pro}$ gene was inserted between DNA sequences that coded sfGFP and 6xHis. The overall sfCiFP-M 6xHis fusion gene was under control of a pBAD promoter. Ampicillin was used as the antibiotic selection marker.

To express sfGFP-$M^{Pro}$-6xHis, E. coli TOP10 cells were transformed with pBAD-sfGFP-$M^{Pro}$. A single colony was selected and grown overnight in 5 mL LB medium with 100 µg/mL ampicillin. On the following day, this starting culture was inoculated into 5 L 2×YT medium with 100 mg/mL ampicillin in 5 separate flasks at 37° C. When the OD reached 0.6, L-arabinose was added (working concentration as 0.2%) to each flask to induce protein expression at 37° C. for 4 hours. Then, the cells were pelleted at 4000 rpm at 4° C., washed with cold PBS, and stored at −80° C. until purification. To purify the expressed protein, frozen cells were re-suspended in a 125 mL buffer containing Tris pH 7.5, 2.5 mM DTT, and L25 mg lysozyme. Resuspended cells were sonicated using a Branson 250 W sonicator with 1 second on, 4 second off, and a total 5 minutes at 60% power output in two rounds. After sonication, the cellular debris were spun down at 16000 rpm for 30 minutes at 4° C. The supernatant was collected and the volume was recorded.

The whole cell lysate analysis indicated that almost all of the fusion protein was hydrolyzed to two separate proteins sfGFP and $M^{Pro}$. An insignificant amount of $M^{Pro}$ was obtained when Ni-NTA resins were used for purification. Therefore, ammonium sulfate precipitation of the whole cell lysate method was performed by the addition of a saturated ammonium sulfate solution at 0° C. The fraction between 30% and 40% of ammonium sulfate was collected. The collected fraction was dissolved in buffer A (20 mM Tris, 10 mM NaCl, and 1 mM DTT at pH 8.0) and dialyzed the obtained solution against the same buffer to remove ammonium sulfate. Thereafter, this solution was subjected to anion exchange column chromatography using Q sepharose resins. Proteins were eluted from the Q sepharose column by applying a gradient with increasing the concentration of buffer B (20 mM Tris, 1 M NaCl, and 1 mM DTT at pH 8.0). The eluted fractions that contained $M^{Pro}$ were concentrated and the concentered solution was subjected to size exclusion chromatography using a HiPrep 16/60 Sephacryl S-100 HR column with a mobile phase containing 10 mM sodium phosphate, 10 mM NaCl, 0.5 mM EDTA and 1 mM DTT at pH 7.8. The final yield of the purified enzyme was 1 mg/L, with respect to the original expression medium volume. The concentration of the final purified $M^{Pro}$ was determined using a Pierce™ 660 nm protein assay and aliquoted as 10 µM $M^{Pro}$ in the size exclusion chromatography buffer for storage at −80° C.

Synthesis of Sub1

The first amino acid (0.5 mmol, 2 equiv.) was loaded manually on chlorotrityl chloride resin (0.52 mmol/g loading) on a 0.25 mmol scale by the addition of DIPEA (3 equivalents). After addition of the first amino acid, automated Fmoc-based solid phases synthesis was performed using a Liberty Blue automated peptide synthesizer. Deprotection of the Fmoc group was carried out with 20% piperidine/DMF. Coupling was performed with a Fmoc-protected amino acid (0.75 mmol, 3.0 equiv.) and the coupling reagent HATU (0.9 mmol, 3.6 equiv.) and DIEA in NMP (1 mmol, 4.0 equiv.). The final amino acid was capped by the addition of 25% acetic anhydride (v/v) in DMF and DIEA (0.2 mmol, 2.0 equiv.).

Coumarin coupling was performed in anhydrous THF using T3P in EtOAc (50% w/v) (3.0 equiv.), DIEA (3 equiv.) and 7-amino-4methyl-coumarin (0.8 equiv.) and mixed for 16 hours. The solvent was removed and the peptide was dissolved in DCM and washed with $H_2O$ (4 times) followed by HCl (2 times) and brine (1 times). The organic layer was dried with $Na_2SO_4$, filtered, and concentrated. Global deprotection was then carried out using triisopropylsilane (5%) and trifluoroacetic acid (30%) v/v in DCM and mixed for 2-3 hours to result in the crude substrate. The peptide was then purified by semi-preparative HPLC and the fractions containing pure product were pooled, concentrated, and analyzed by LC-MS for purity.

Synthesis of Sub2

Automated Fmoc-based solid phase synthesis was performed on a Liberty Blue automated peptide synthesizer. Synthesis was conducted on a 0.1 mmol scale with Fmoc Rink amide MBHA resin (0.52 mmol/g loading) and 3 equivalents of protected amino acids. Deprotection of the Fmoc group was carried out with 20% piperidine/DMF. Coupling was done using the desired Fmoc-protected amino acid (0.2 mmol, 2.0 equiv.), coupling reagent Oxyma (0.4 mmol, 4.0 equiv.) and DIC (0.4 mmol, 4.0 equiv.). After the final amino acid had been coupled, the resin was washed trice with DMF and DCM. Cleavage from the resin was performed using trifluoroacetic acid (95%), triisopropylsilane (2.5%), and water (2.5%) with agitation for 4 hours. The peptide was drained into cold methyl tert-butyl ether where it precipitated out. The precipitate was centrifuged, mother liquor was decanted, the pellet was dissolved in DMF, and then the peptide was purified by LCMS.

To express $M^{Pro}$ for experimental characterizations of 29 selected small molecule medicines, the $M^{Pro}$ gene was fused to a superfolder green fluorescent protein (sfGFP) gene and a 6xHis tag at its 5' and 3' ends respectively in a pBAD-sfGFP plasmid that we used previously in the lab. SfGFP can stabilize proteins following genetic fusion. A TEV protease cleavage site was designed between sfGFP and $M^{Pro}$ for the TEV-catalyzed proteolytic release of $M^{Pro}$ from sfGFP after expression and purification of the fusion protein. The 6xHis tag was placed right after the $M^{Pro}$ C-terminus for straightforward purification with Ni-NTA resins.

It was believed that the TEV protease cleavage of sfGFP would activate $M^{Pro}$ to cleave the C-terminal 6xHis tag so that a finally intact $M^{Pro}$ protein could be obtained. However, after carrying out expression in E. coli TOP10 cells, a minimal amount of the fusion protein was able to be purified. Analysis of the cell lysate indicated that cleavage of a substantial amount of $M^{Pro}$ from sfGFP. It was believed that since enriching the cleaved $M^{Pro}$ using Ni-NTA resins was not possible, the C-terminal 6xHis tag was apparently cleaved as well. TEV protease is a cysteine protease that cleaves after the Gln residue in the sequence Glu-Asn-Leu-Tyr-Phe-Gln-(Gly/Ser) and $M^{Pro}$ is known to cleave the sequence Thr-ValLeu-Gln-(Gly/Ser), thus the two cleavage sites share a same P1 residue. Accordingly, $M^{Pro}$ is able to efficiently cleave the TEV protease cutting site to maturate inside E. coli cells and thus it is likely that $M^{Pro}$ has a higher substrate promiscuity than the SARS-CoV-1 enzyme.

To purify the cleaved and maturated $M^{Pro}$, ammonium sulfate was used to precipitate it from cell lysate and the ion exchange and size exclusion chromatography were utilized to isolate $M^{Pro}$ to more than 95% purity. A fluorogenic coumarin-based hexapeptide substrate (Sub1) and a FRET-based decapeptide substrate (Sub2) were designed and synthesized and a commercial FRET-based tetradecapeptide substrate (Sub3) was acquired (see FIG. 1A).

Testing of enzyme activities on the three substrates indicated that the enzyme had low activity toward Sub1 (FIG. 1B) and enzyme activity on Sub3 was higher than that on Sub2 (FIG. 1C) under the assay conditions. Thereafter, Sub3 was used in all subsequent inhibition analysis.

To identify an optimal enzyme concentration for use in inhibition analysis, activities of different concentrations of $M^{Pro}$ were tested on 10 µM Sub3. The detected catalytic rate of the Sub3 cleavage was not proportional to the enzyme concentration (FIG. 1D). When the enzyme concentration decreased from 50 nM to 10 nM, the Sub3 cleavage rate was approximately decreased roughly proportional to the square of the concentration decrease, suggesting characteristics of second-order kinetics. This observation indicates that the enzyme needs to dimerize in order to be active. In all following assays, 50 nM $M^{Pro}$ and 10 µM Sub3 were used throughout.

Example 3

Evaluation of $M^{Pro}$ Inhibition by Various Compositions

For the instant example, 29 small molecule compositions were purchased from commercial providers without further purification and characterization. In addition, the investigational antiviral medicine rupintrivir (a 3C protease inhibitor) was obtained and this composition was also evaluated in the instant example.

With the exception of itraconazole (which has low solubility in DMSO), the compositions were dissolved in DMSO to make 5 mM stock solutions and proceeded to use these stock solutions to evaluate $M^{Pro}$ inhibition. The compositions were diluted to a final concentration of 1 mM in the inhibition assay conditions, except that itraconazole had a final concentration of 0.14 mM due to its low solubility in DMSO. A value of 20% DMSO was maintained in the final assay condition to prevent compositions from precipitating.

The final screening assay conditions included 50 nM $M^{Pro}$, 10 µM Sub3, and 1 mM of the tested composition. Enzyme stock and substrate stock solutions were diluted using a buffer containing 10 mM sodium phosphate, 10 mM NaCl, and 0.5 mM EDTA at pH 7.8 for achieving desired final concentrations. For a control group, an $M^{Pro}$ activity assay in the absence of a composition (blank) was made for comparison. Triplicate repeats were carried out for control and the tested compositions.

Assays were run in triplicates. First, 30 µL of a 1.67 nM $M^{Pro}$ solution was added to each well in a 96-well plate and then 20 µL of 5 mM stock solutions of compositions in DMSO was provided. The plates were briefly shaken and then incubated at 37° C. for 30 minutes. Thereafter, 50 µL of a 20 µM Sub3 solution was added to initiate the activity analysis. The EDANS fluorescence with excitation at 336 nm and emission at 455 nm the cleaved substrate were detected. The fluorescence increasing slopes were determined at the initial 5 minutes and then normalized with respect to the control.

FIG. 2 shows results of the instant example. As shown in FIG. 2, approximately half of the tested compositions demonstrated strong inhibition of $M^{Pro}$ at a concentration of 1 mM (itraconazole at 0.14 mM due to its low solubility in DMSO). This finding supports the practical use of a docking method in guiding research of compositions to treat COVID-19.

Furthermore, FIG. 2 shows that several compositions, including fexofenadine, indinavir, pirenzepine, reboxetine, and doxapram, demonstrated activation of $M^{Pro}$ (>15%). This result was contrary to the prediction of the docking analysis and suggests caution for repurposing known drugs to treat COVID-19 prior to thorough investigation of their SARS-CoV-2 biology.

Example 4

Further Evaluation of $M^{Pro}$ Inhibition by Various Compositions

For the instant example, 17 small molecule compositions plus rupintrivir were selected to undergo further evaluation. Each of the 18 compositions displayed strong inhibition of $M^{Pro}$. The instant example provides further characterization of the $IC_{50}$ values for $M^{Pro}$ inhibition of the compositions by varying the composition concentrations from 1 µM to 10 mM.

The final inhibition assay conditions contained 50 nM $M^{Pro}$, 10 µM Sub3, and a varying concentration of a composition. Similar to Example 3, enzyme stock and substrate stock solutions were diluted using a buffer containing 10 mM sodium phosphate, 10 mM NaCl, and 0.5 mM EDTA at pH 7.8 for achieving desired final concentrations. Assays were run in triplicates.

For the inhibition analysis, 30 µL of a 167 nM $M^{Pro}$ solution was added to each well in a 96-well plate and then 20 µL of inhibitor solutions with varying concentrations in DMSO was provided. The plates were briefly shaken and then incubated at 37° C. for 30 minutes. Thereafter, 50 µL of a 20 µM Sub3 solution was added to initiate the activity analysis. The fluorescence signal was monitored and processed the initial slopes as described in Example 3. Thereafter, GraphPad 8.0 was used to analyze the data and the [Inhibitor] vs. response—Variable slope (four parameters) fitting was utilized to determine both $IC_{50}$ and Hill coefficient values.

Figure 3:
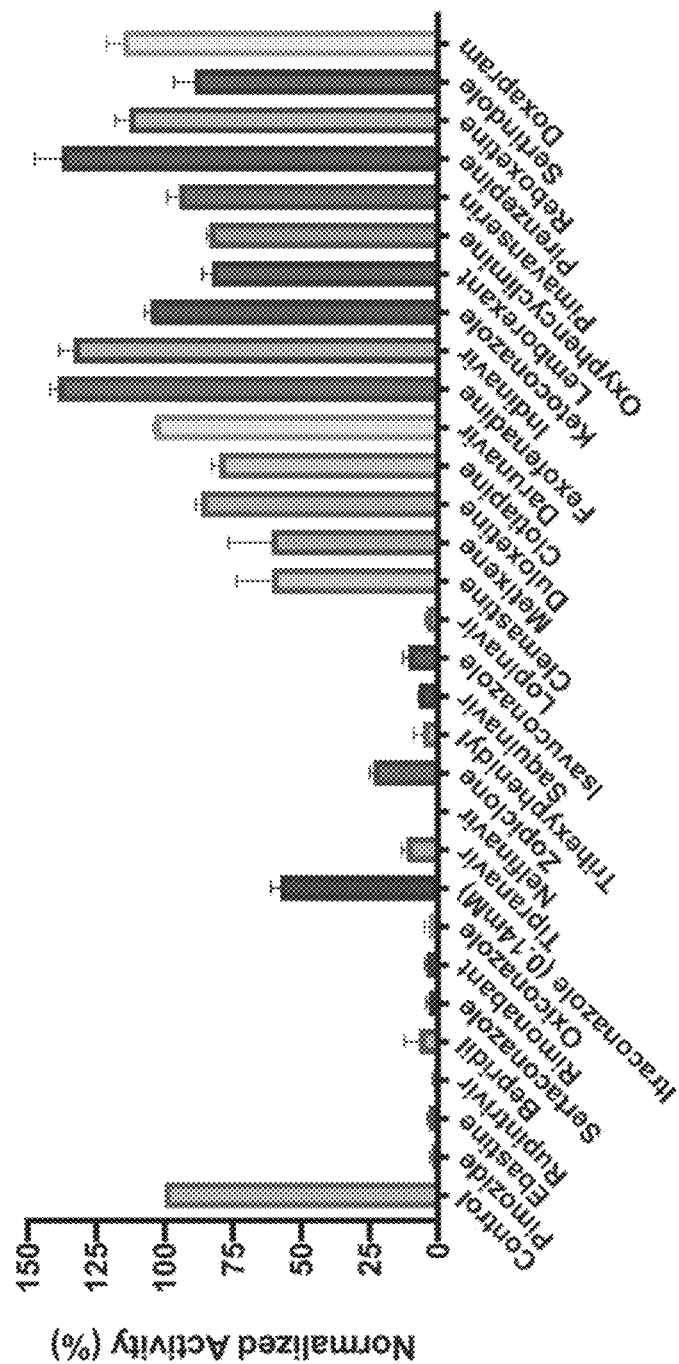
FIG. 3 shows the results of the initial screening of $M^{Pro}$ inhibition by various compositions. For each composition, 1 mM was used to perform the $M^{Pro}$ inhibition assay (0.14 mM was used for itraconazole due to its low solubility in DMSO). Fluorescence intensity was normalized for the control (blank). Triplicate experiments were performed for each composition. Values are presented as mean±standard error (SE).

FIG. 3 shows results of the instant example. As shown in FIG. 3, seven compositions (pimozide, ebastine, rupintrivir, bepridil, sertaconazole, rimonabant, and oxiconazole) demonstrated an $IC_{50}$ value below 100 µM. In particular, pimozide, ebastine, and bepridil were the most potent, with $IC_{50}$ values of 42±2, 57±12, and 72±12 µM, respectively.

Furthermore, rupintrivir demonstrated an $IC_{50}$ value of 68±7 µM. In comparison, other antiviral compositions have higher $IC_{50}$ values for inhibiting $M^{Pro}$, such as about 500 µM for lopinavir and 234±5 µM for nelfinavir.

Figure 4:
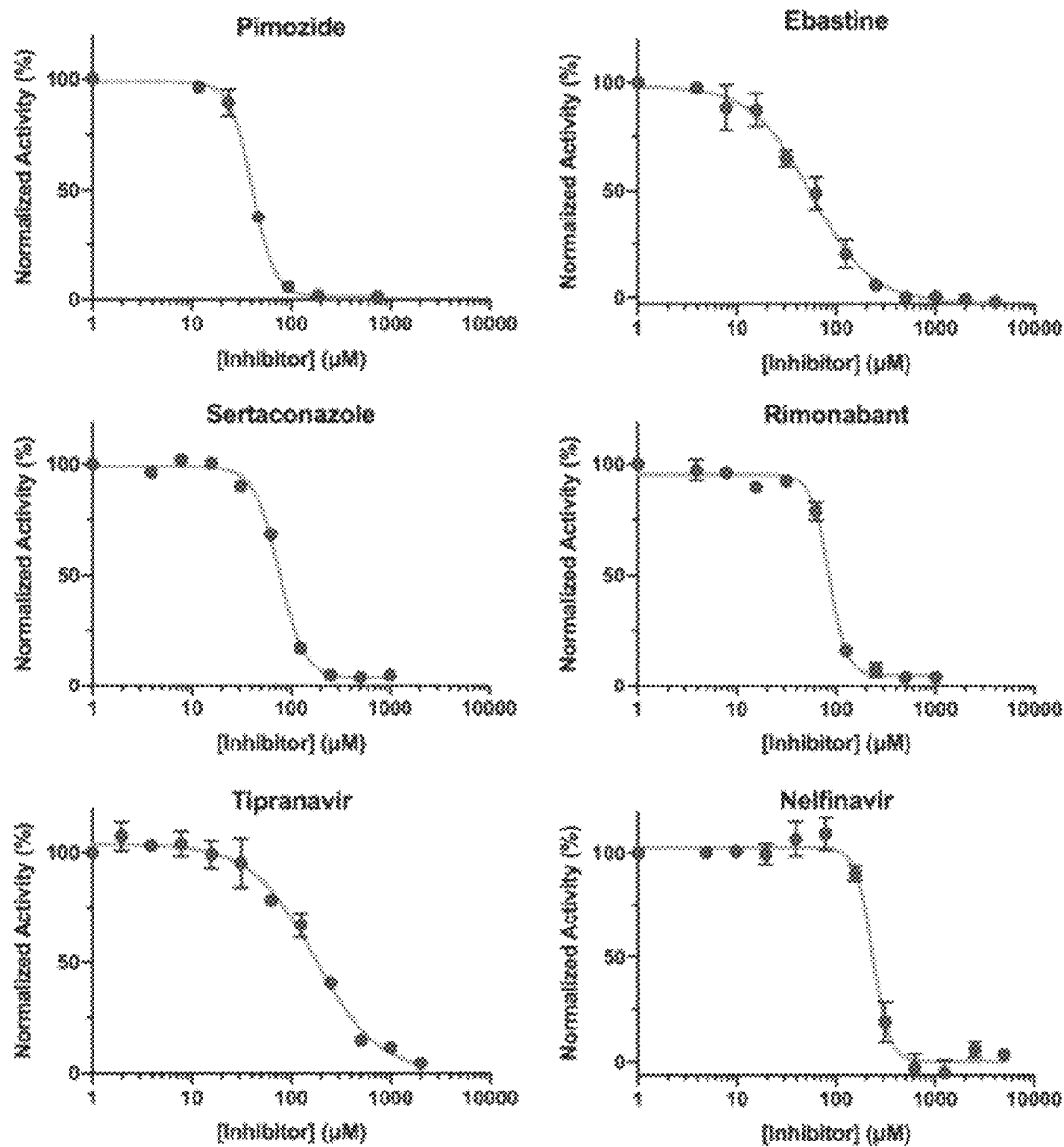
FIG. 4 shows the results of $IC_{50}$ assays for 18 of the compositions regarding $M^{Pro}$ inhibition. Triplicate experiments were performed for each composition. The $IC_{50}$ values are presented as mean±standard error (SE). GraphPad Prism 8.0 was used to perform data analysis.
Figures 5A, 5B, 5C, 5D:
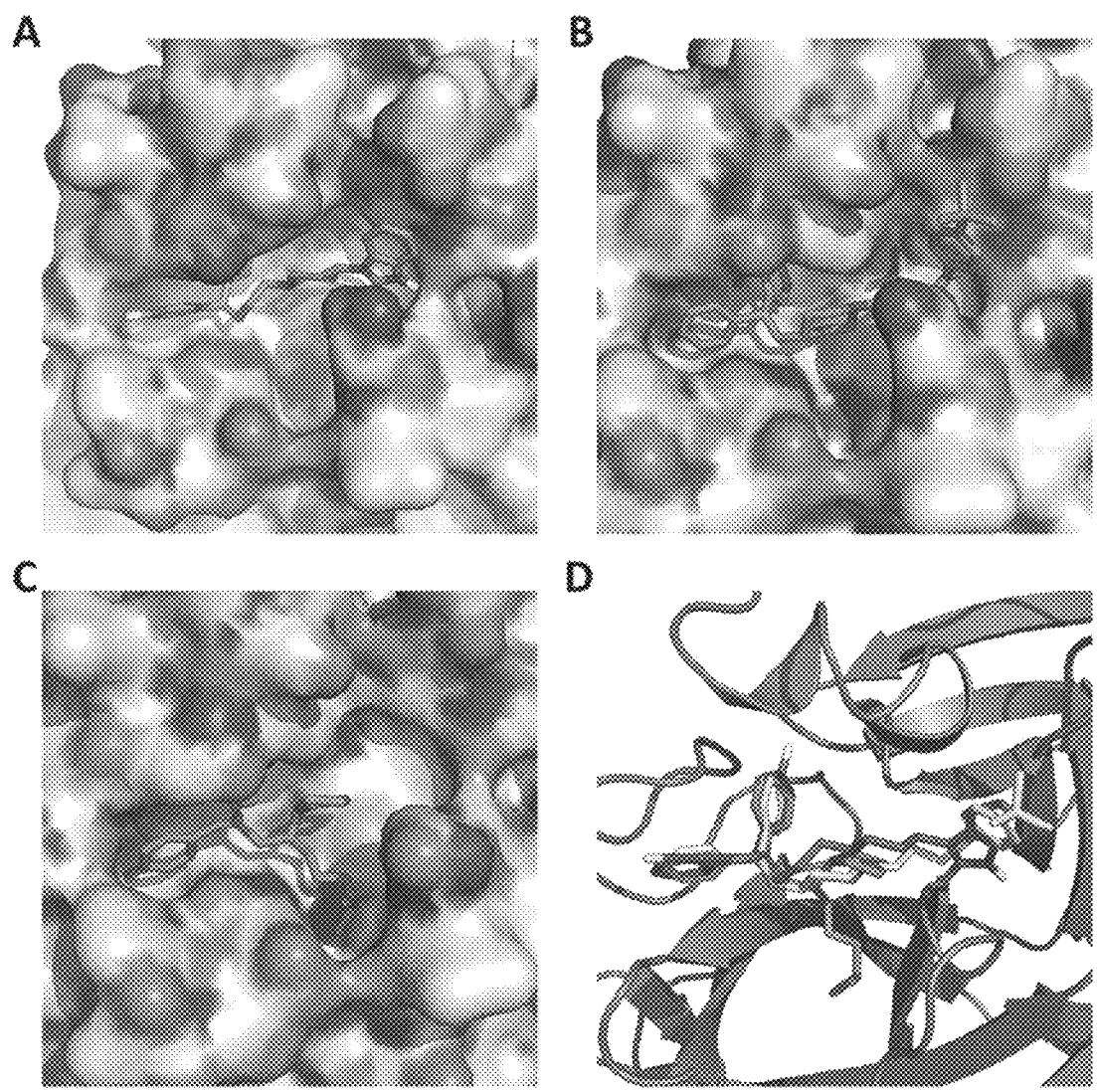
FIGS. 5A-5D show docking results for three of the tested compositions.

FIG. 4 demonstrates large variations in Hill coefficients of $IC_{50}$ curves for the various tested compositions. Table 2 summarizes $IC_{50}$ values and Hill coefficients for the tested compositions. As shown in Table 2, duloxetine and zopiclone demonstrated the two highest Hill coefficients, with a gradual $M^{Pro}$ activity decrease over an increasing inhibitor concentration. To the contrary, saquinavir and lopinavir demonstrated the lowest Hill coefficients with highly steep $IC_{50}$ curves.

TABLE 2

$IC_{50}$ and Hill coefficient values of 18 tested compositions

| Name | $IC_{50}$ (µM) | Hill Slope |
|---|---|---|
| Pimozide | 42 ± 2 | 3.1 ± 0.4 |
| Ebastine | 57 ± 12 | 1.5 ± 0.2 |
| Rupintrivir | 68 ± 7 | 1.4 ± 0.2 |
| Bepridil | 72 ± 3 | 2.9 ± 1.0 |
| Sertaconazole | 76 ± 2 | 3.5 ± 0.2 |
| Rimonabant | 85 ± 3 | 5.0 ± 0.4 |
| Oxiconazole | 99 ± 6 | 3.8 ± 0.4 |
| Itraconazole | 111 ± 35 | 1.6 ± 0.2 |
| Tipranavir | 180 ± 20 | 1.4 ± 0.2 |
| Nelfinavir | 234 ± 15 | 5.4 ± 1.0 |
| Zopiclone | 349 ± 77 | 1.2 ± 0.2 |
| Trihexyphenidyl | 370 ± 53 | 8.9 ± 6.4 |
| Saquinavir | 411 ± 6 | 26.8 ± 2.6 |
| Isavuconazole | 438 ± 11 | 5.2 ± 0.7 |
| Lopinavir | 486 ± 2 | 29.9 ± 2.4 |
| Clemastine | 497 ± 148 | 11.2 ± 7.3 |
| Metixene | 635 ± 43 | 8.7 ± 5 |
| Duloxetine | 3047 ± 634 | 0.93 ± 0.07 |

The two most potent compositions tested in the instant example were pimozide and ebastine. Structurally, pimozide and ebastine both comprise a diphenylmethyl moiety. Furthermore, bepridil comprises a spatially similar structure moiety, N-phenyl-N-benzylamine. The docking analysis described herein suggests a similar binding mode for these three compositions, given the similar (see FIGS. 5A-5D). The two aromatic rings occupy the enzyme pockets that associate with the P2 and P4 residues in a substrate. This observation is in line with a crystallographic study that showed two aromatic rings with a single methylene linker bound to the active site of the SARS-CoV-1 enzyme. It is believed that the inclusion of the diphenylmethyl moiety in structure-activity relationship studies of $M^{Pro}$-targeting ligands is important for potent and high cell-permeable $M^{Pro}$ inhibitors.

Example 5

Cellular SARS-CoV-2 Assays of Various Compositions

The three compositions with the most potent $IC_{50}$ values for inhibiting $M^{Pro}$ were bepridil, pimozide, and ebastine.

The instant example evaluates the ability of the compositions to raise endosomal pH, which is believed to significantly impact activities of endosomal proteases that may be required to process SARS-CoV-2 membrane proteins.

For the instant example, a live virus-based microneutralization (MN) assay was conducted to evaluate the efficacy of pimozide, ebastine and bepridil for inhibition of SARS-CoV-2 infection in Vero E6 cells. Vero E6 is a cell line isolated kidney epithelial cells from African Green Monkey.

A slightly modified MN assay was used as previously described to rapidly evaluate the drug efficacy against SARS-CoV-2 infection in Vero E6 and ACE2-expressing A549 cell cultures. See, e.g., Agrawal A S, et al. (2016) Passive Transfer of A Germline-like Neutralizing Human Monoclonal Antibody Protects Transgenic Mice Against Lethal Middle East Respiratory Syndrome Coronavirus Infection. *Sci Rep* 6:31629; Du L, et al. (2013) A truncated receptor-binding domain of MERS-CoV spike protein potently inhibits MERS-CoV infection and induces strong neutralizing antibody responses: implication for developing therapeutics and vaccines. *PLoS One* 8(12):e81587; Du L, et al. (2014) A conformation-dependent neutralizing monoclonal antibody specifically targeting receptor-binding domain in Middle East respiratory syndrome coronavirus spike protein. *J Virol* 88(12):7045-7053.

Confluent Vero E6 cells grown in 96-wells microtiter plates were pre-treated with serially 2-folds diluted individual drugs in duplicate over eight concentrations for two hours before infection with ~100 infectious SARS-CoV-2 particles in 100 μL EMEM supplemented with PBS. Vero E6 cells treated with parallel diluted dimethyl sulfoxide (DMSO), with or without virus, were included as positive and negative controls, respectively. After cultivation at 37° C. for 4 days, individual wells were observed under the microcopy to evaluate the status of virus-induced formation of cytopathogenic effect (CPE). The efficacy of the tested compositions was calculated and expressed as the lowest concentration capable of completely preventing virus-induced CPE in 100% of the wells. The toxicity to the treated cells was assessed by observing floating cells and altered morphology of adhered Vero E6 cells in wells under the microcopy. All tested compositions were dissolved in 100% DMSO as 10 mM stock solutions and diluted in culture media.

Three compositions—bepridil, pimozide, and ebastine—were tested in a concentration range from 0.16 to 200 μM. Cytopathogenic effect (CPE) was observed for pimozide and ebastine at all tested concentrations. Furthermore, bepridil completely prevented SARS-CoV-2-induced CPE in Vero E6 cells when the concentration reached 5 μM and also inhibited CPE in a dose dependent manner below 5 μM (see Table 3). Bepridil did not display cellular toxicity until the concentration reached 50 μM.

TABLE 3

SARS-CoV-2 induced CPE in Vero E6 cells in the presence of bepridil.

| Bepridil (μM) | Repeat 1 | Repeat 2 |
|---|---|---|
| 200 | $C^a$ | C |
| 100 | C | C |
| 50 | C | C |
| 20 | $ND^b$ | ND |
| 10 | ND | ND |
| 5 | ND | ND |
| 2.5 | CPE | CPE |
| 1.25 | CPE | CPE |
| 0.62 | CPE | CPE |
| 0.31 | CPE | CPE |
| 0.16 | CPE | CPE |

$^a$Cytotoxicity;
$^b$Both cytotoxicity and CPE are not detected.

A parallel test in ACE2-expressing A549 cells derived from human alveolar epithelial cells demonstrated that bepridil prevented SARS-CoV-2-induced CPE completely at 6.25 μM (see Table 4). Further, bepridil inhibited CPE in a dose dependent manner below 6.25 μM but did not display a cytotoxic effect when the concentration reached 200 μM.

TABLE 4

SARS-CoV-2 induced CPE in ACE2-expressing A549 cells in the presence of bepridil.

| Bepridil (μM) | Repeat 1 | Repeat 2 |
|---|---|---|
| 200 | ND | ND |
| 100 | ND | ND |
| 50 | ND | ND |
| 25 | ND | ND |
| 12.5 | ND | ND |
| 6.25 | ND | ND |
| 3.12 | CPE | CPE |
| 1.56 | CPE | CPE |

The complete prevention of SARS-CoV-2-induced CPE in Vero E6 and ACE2-expressing A549 cells by bepridil at a concentration much lower than its $IC_{50}$ value for inhibiting $M^{Pro}$ may be due to its dual function against SARS-CoV-2. Without being bound by any theory, the ability of bepridil to inhibit $M^{Pro}$ and to raise the pH of endosomes may reduce viral replication of SARS-CoV-2 in host cells and demonstrate efficacy in treating COVID-19 patients.

Bepridil is a calcium channel blocker with a significant anti-anginal activity and was previously used at a dose of 12 mg/kg for the treatment of Ebola virus infections. For patients with chronic stable angina, the recommended daily dose of bepridil is 200-400 mg. Moreover, mice administered bepridil at a dose as high as 300 mg/kg/day did not show alteration in mating behavior and reproductive performance, indicating that bepridil has very low toxicity.

In patients, bepridil can reach a state $C_{max}$ of 3.72 μM. Based on the virus microneutralization analysis, this concentration is effective for inhibition of SARS-CoV-2. Collectively, the results described herein indicate that bepridil is unexpectedly effective in both preventing SARS-CoV-2 from entry into mammalian cell hosts and preventing SARS-CoV-2 replication in mammalian cell hosts.

What is claimed is:

1. A method of treating COVID-19 in a patient in need thereof, said method comprising the step of administering a pharmaceutical composition comprising bepridil to the patient, wherein the pharmaceutical composition provides inhibition of severe acute respiratory syndrome-coronavirus 2 (SARS-CoV-2) main protease ($M^{Pro}$).

2. The method of claim 1, wherein COVID-19 is caused by infection with SARS-CoV-2 or a mutation of SARS-CoV-2.

3. The method of claim 1, wherein the patient has severe COVID-19-related symptoms.

4. The method of claim 1, wherein the patient has mild COVID-19-related symptoms.

5. The method of claim 1, wherein the patient is asymptomatic for COVID-19-related symptoms but has been infected with SARS-CoV-2.

6. The method of claim 1, wherein the patient is at high risk for infection with SARS-CoV-2.

7. The method of claim 1, wherein the treatment is a prophylactic treatment of the patient prior to infection with SARS-CoV-2.

* * * * *